US011969057B2

(12) United States Patent
Kim

(10) Patent No.: US 11,969,057 B2
(45) Date of Patent: Apr. 30, 2024

(54) SOLE FOR FOOTWEAR WITH POSITIONING FACES

(71) Applicant: Vidar Licensing Inc., Toronto (CA)

(72) Inventor: Sun Ho Kim, Toronto (CA)

(73) Assignee: Vidar Licensing Inc., Toronto (CA)

( * ) Notice: Subject to any disclaimer, the term of this patent is extended or adjusted under 35 U.S.C. 154(b) by 153 days.

(21) Appl. No.: 17/112,381

(22) Filed: Dec. 4, 2020

(65) Prior Publication Data

US 2021/0100312 A1 Apr. 8, 2021

Related U.S. Application Data

(63) Continuation of application No. PCT/CA2019/050788, filed on Jun. 6, 2019.

(60) Provisional application No. 62/681,210, filed on Jun. 6, 2018.

(51) Int. Cl.
| | |
|---|---|
| A43B 7/24 | (2006.01) |
| A43B 5/00 | (2022.01) |
| A43B 7/1405 | (2022.01) |
| A43B 7/1425 | (2022.01) |
| A43B 13/14 | (2006.01) |

(52) U.S. Cl.
CPC .............. *A43B 7/1405* (2013.01); *A43B 5/00* (2013.01); *A43B 7/1425* (2013.01); *A43B 7/24* (2013.01); *A43B 13/143* (2013.01)

(58) Field of Classification Search
CPC ... A43B 7/1405; A43B 7/1415; A43B 7/1425; A43B 7/145; A43B 13/143; A43B 7/24
USPC ................................. 36/25 R, 142, 143, 144
See application file for complete search history.

(56) References Cited

U.S. PATENT DOCUMENTS

| | | | | |
|---|---|---|---|---|
| 3,958,578 A | * | 5/1976 | Tennant .................... | A43B 7/00 482/79 |
| 4,425,721 A | * | 1/1984 | Spronken ............... | A43B 3/128 36/86 |
| 5,507,106 A | * | 4/1996 | Fox ...................... | A43B 13/143 36/114 |
| 5,579,591 A | * | 12/1996 | Kousaka .............. | A43B 13/143 36/31 |

(Continued)

FOREIGN PATENT DOCUMENTS

| | | |
|---|---|---|
| FR | 2912294 A1 | 8/2008 |
| WO | 2012001685 A1 | 1/2012 |

OTHER PUBLICATIONS

Chirvase, L.; Supplementary Search Report from corresponding European Application No. 19816088.9; search completed Feb. 3, 2022.

(Continued)

*Primary Examiner* — Marie D Bays
(74) *Attorney, Agent, or Firm* — Laurie Wright; Christopher N. Hunter; Blake, Cassels & Graydon LLP

(57) ABSTRACT

There is provided a sole for footwear with a bottom surface comprising: a primary surface and one or more positioning face, wherein: the one or more positioning faces are at an angle to the primary surface; engaging a ground with the primary surface causes a wearer of the footwear to take a natural stance; engaging the ground with the one or more positioning faces causes the wearer to take one or more athletic stances; and the wearer switches between the natural stance and the one or more athletic stances by shifting their weight.

16 Claims, 44 Drawing Sheets

(56) References Cited

U.S. PATENT DOCUMENTS

| | | | | |
|---|---|---|---|---|
| 5,826,351 A * | 10/1998 | Tsuji | A43B 13/148 36/31 |
| 5,940,992 A * | 8/1999 | Darby | A43B 13/148 36/76 R |
| 5,974,699 A * | 11/1999 | Park | A43B 13/148 36/103 |
| 6,260,289 B1 * | 7/2001 | Tsuji | A43B 13/148 36/31 |
| 6,341,432 B1 | 1/2002 | Muller | |
| 6,349,487 B1 * | 2/2002 | Hice | A43B 13/143 36/43 |
| 6,698,050 B1 * | 3/2004 | Frye | A43B 7/1435 12/133 B |
| 7,278,227 B2 * | 10/2007 | Masoodifar | A43B 13/148 482/79 |
| 7,533,476 B2 | 5/2009 | Hay | |
| 8,387,278 B2 * | 3/2013 | Rees | A43B 13/143 36/103 |
| 8,707,586 B2 * | 4/2014 | Adair | A43B 13/26 36/67 R |
| 8,938,893 B2 * | 1/2015 | Adair | A43B 7/144 36/144 |
| 9,717,302 B2 | 8/2017 | Adair et al. | |
| 9,788,600 B2 | 10/2017 | Wawrousek et al. | |
| 9,857,788 B2 | 1/2018 | Piontkowski | |
| 2002/0157279 A1 * | 10/2002 | Matsuura | A43B 13/143 36/103 |
| 2004/0040181 A1 * | 3/2004 | Kim | A43B 5/001 36/144 |
| 2004/0064973 A1 * | 4/2004 | Talbott | A43B 13/12 36/114 |
| 2009/0199432 A1 * | 8/2009 | Park | A43B 7/24 36/25 R |
| 2009/0282700 A1 | 11/2009 | Dillon | |
| 2010/0192416 A1 * | 8/2010 | Rees | A43B 13/145 36/103 |
| 2010/0307025 A1 | 12/2010 | Truelsen et al. | |
| 2012/0023774 A1 | 2/2012 | Garcia | |
| 2012/0079740 A1 | 4/2012 | Zhou | |
| 2012/0227285 A1 * | 9/2012 | Adair | A43C 1/00 36/114 |
| 2012/0246976 A1 * | 10/2012 | Weiler | A43B 13/146 36/25 R |
| 2013/0291405 A1 * | 11/2013 | Adair | A43C 1/04 36/115 |

OTHER PUBLICATIONS

Santella, L.; International Search Report from corresponding PCT Application No. PCT/CA2019/050788; search completed Aug. 27, 2019.

* cited by examiner

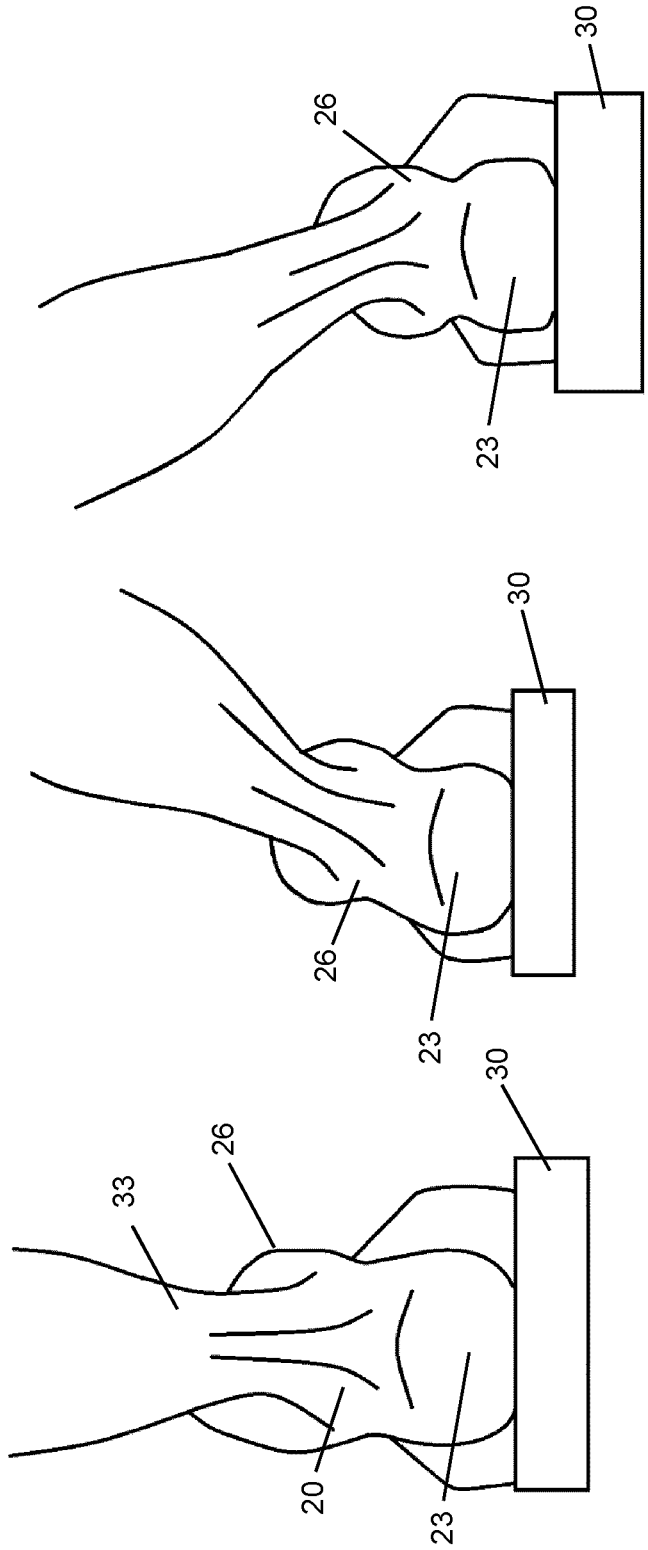

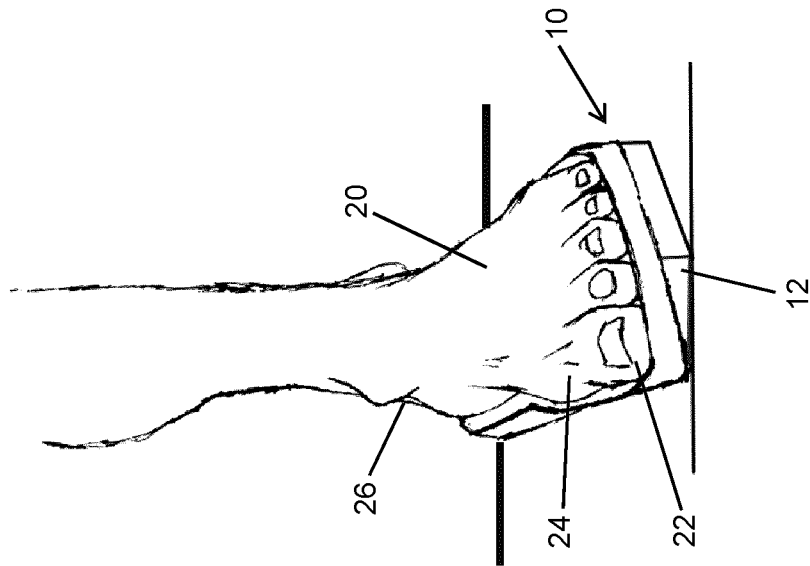
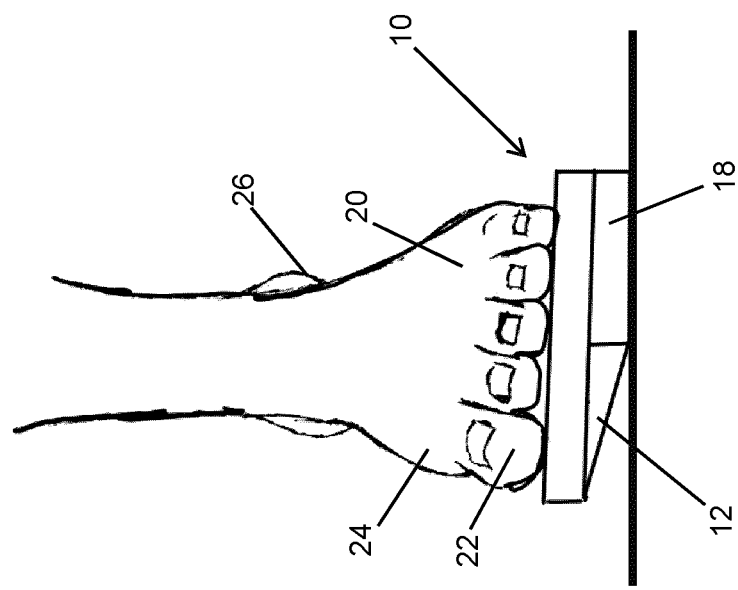

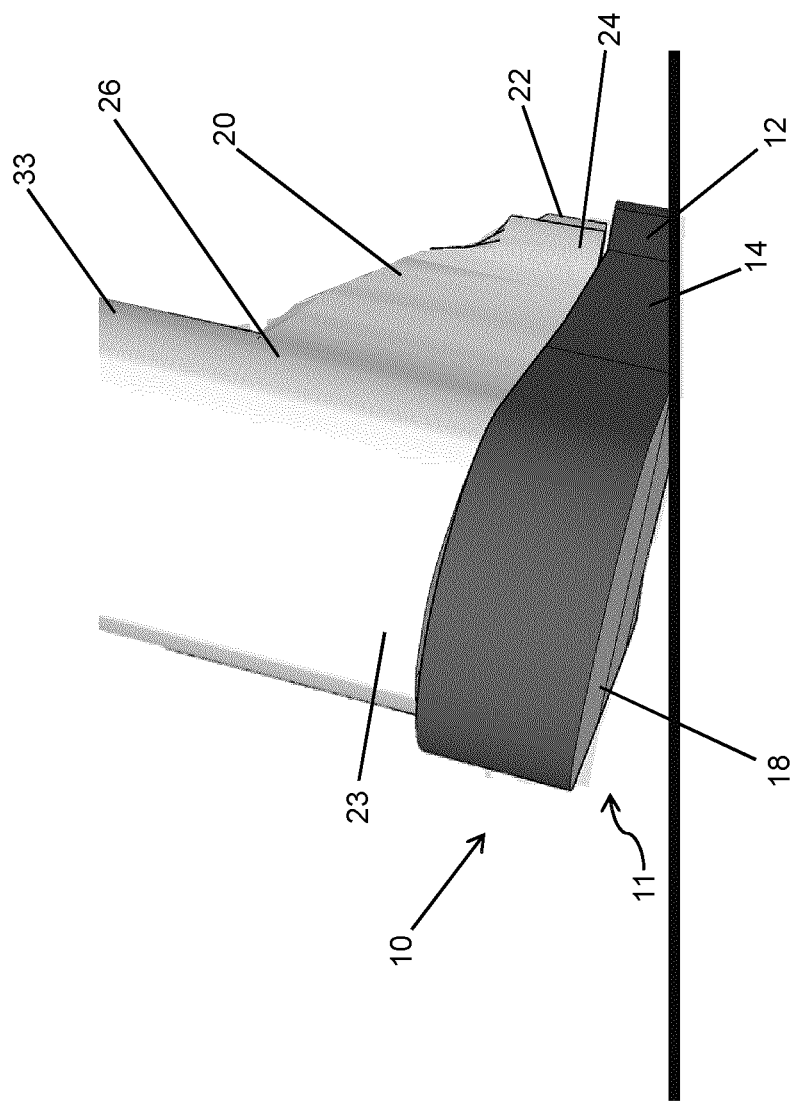

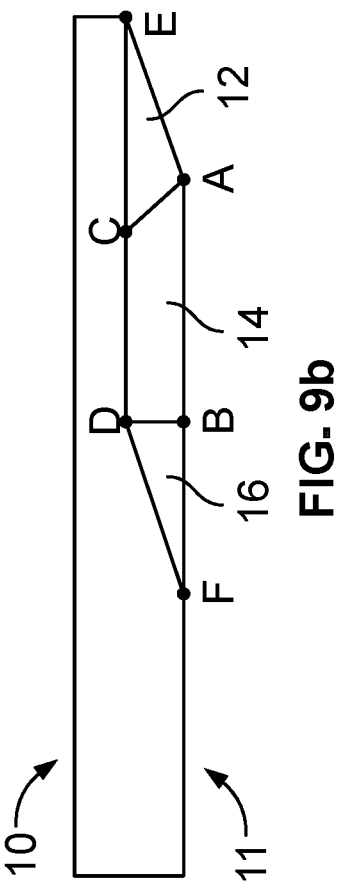
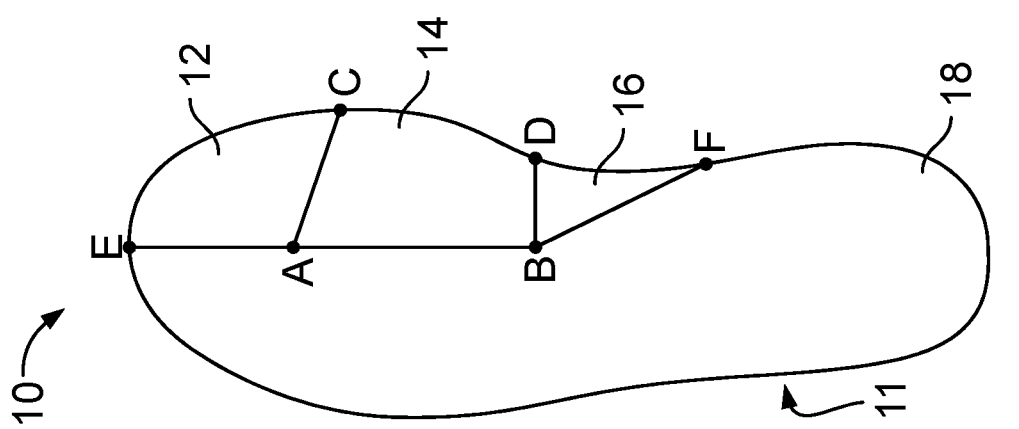
FIG. 9b
FIG. 9a

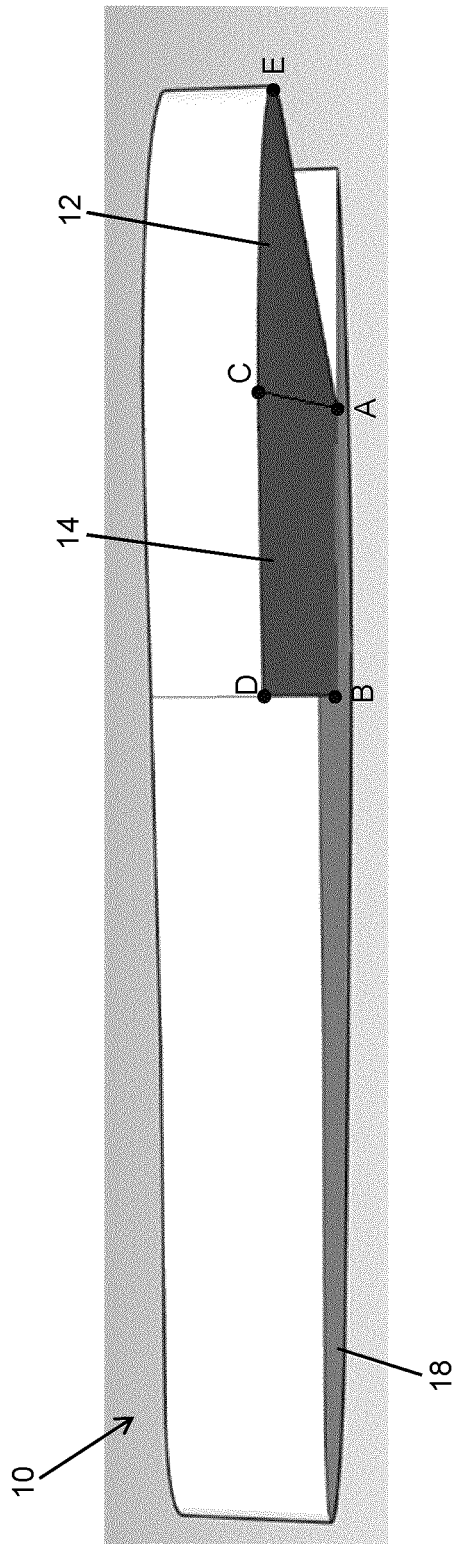
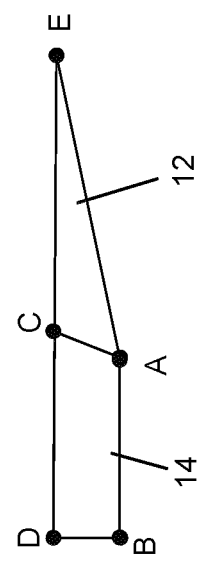
FIG. 12(a)
FIG. 12(b)

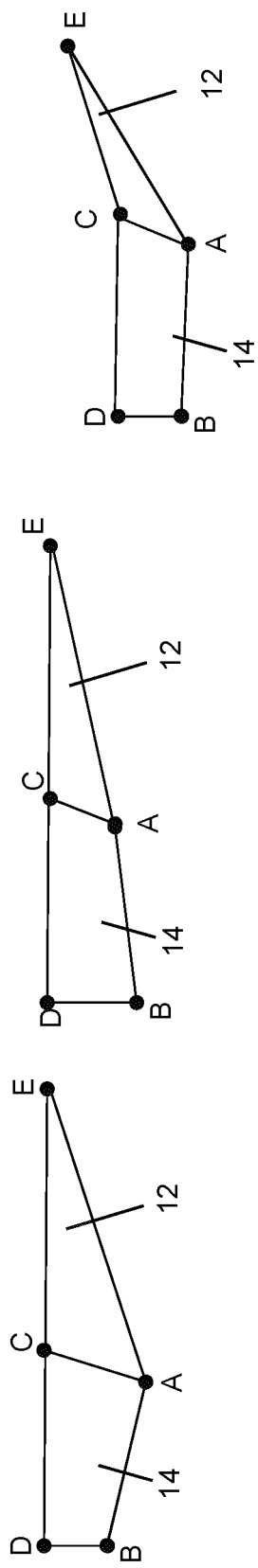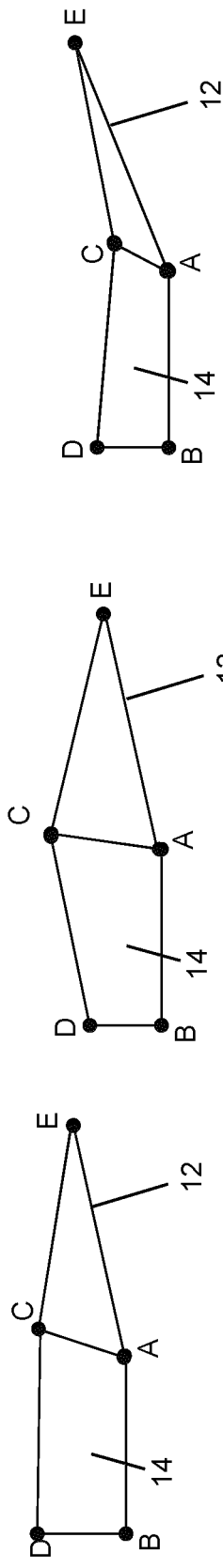

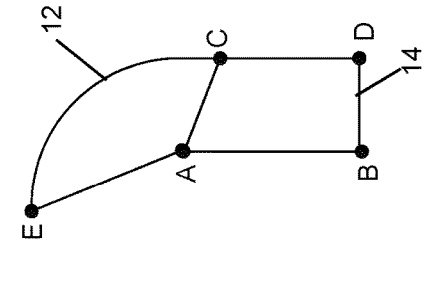
FIG. 13(d)
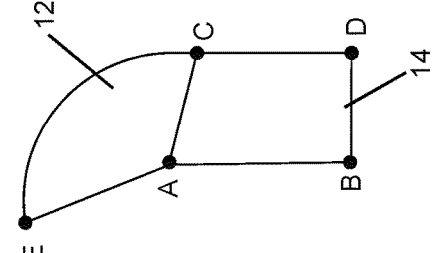
FIG. 13(h)
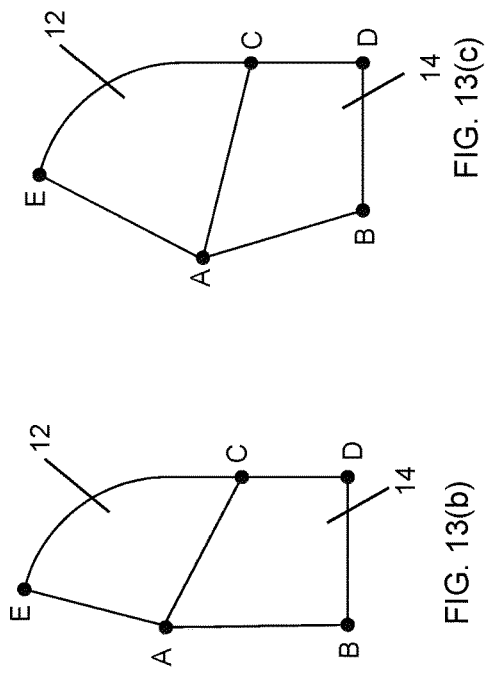
FIG. 13(c)
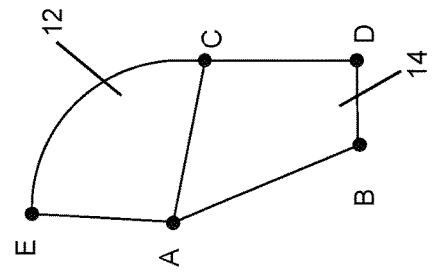
FIG. 13(g)
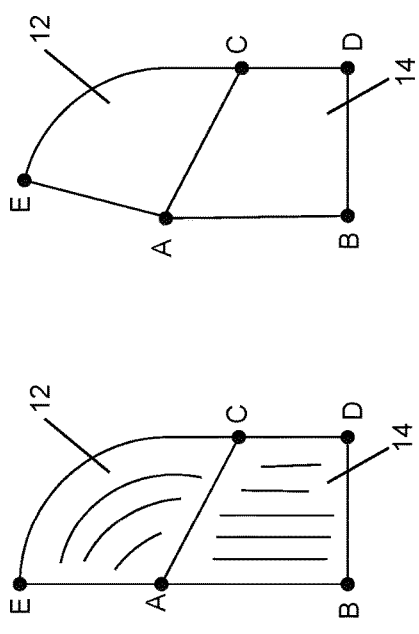
FIG. 13(b)
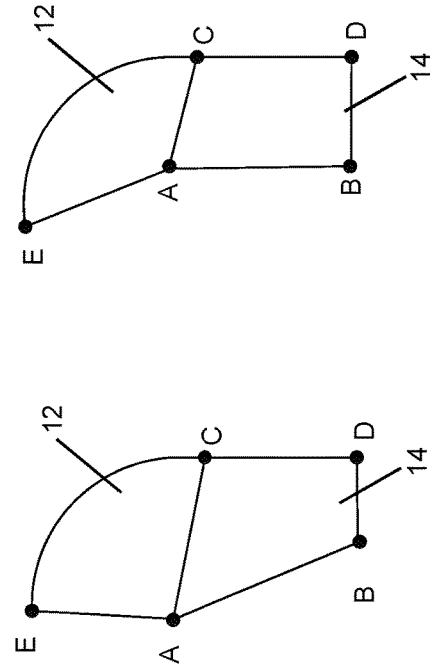
FIG. 13(f)
FIG. 13(a)
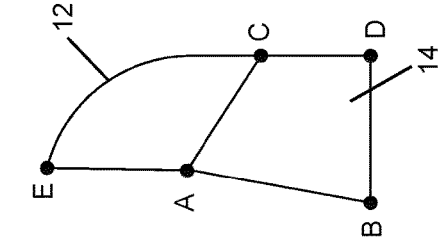
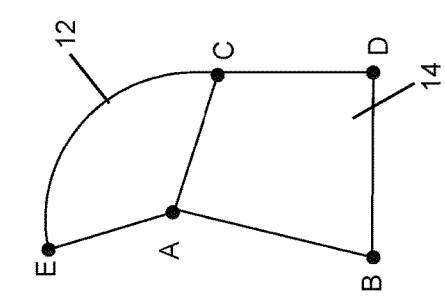
FIG. 13(e)

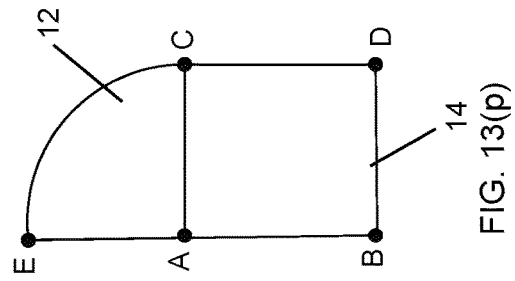
FIG. 13(p)
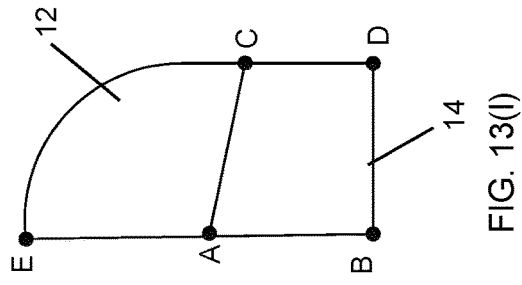
FIG. 13(l)
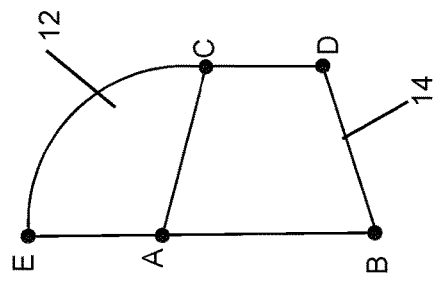
FIG. 13(o)
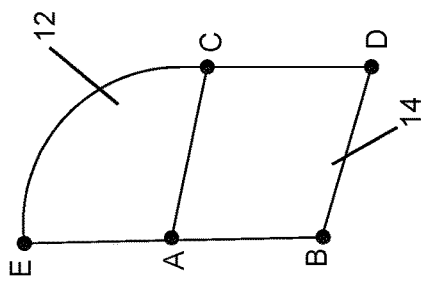
FIG. 13(k)
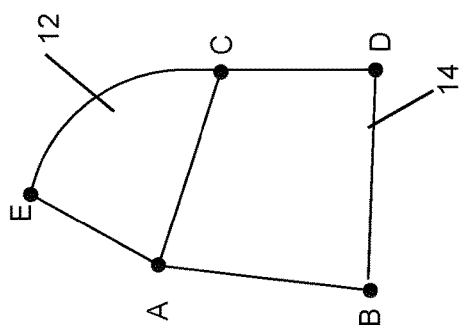
FIG. 13(n)
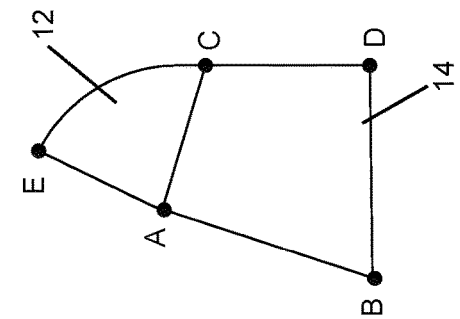
FIG. 13(j)
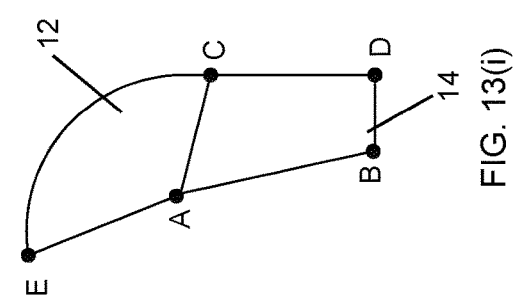
FIG. 13(m)
FIG. 13(i)

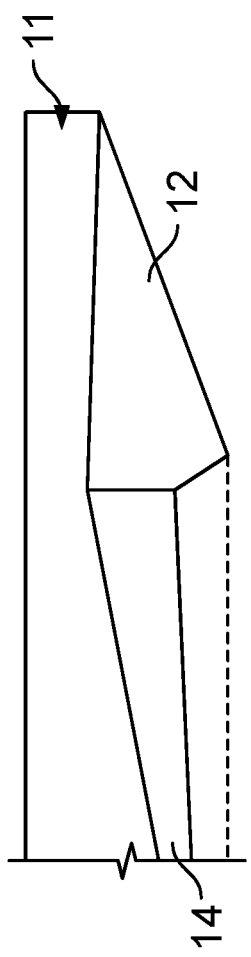
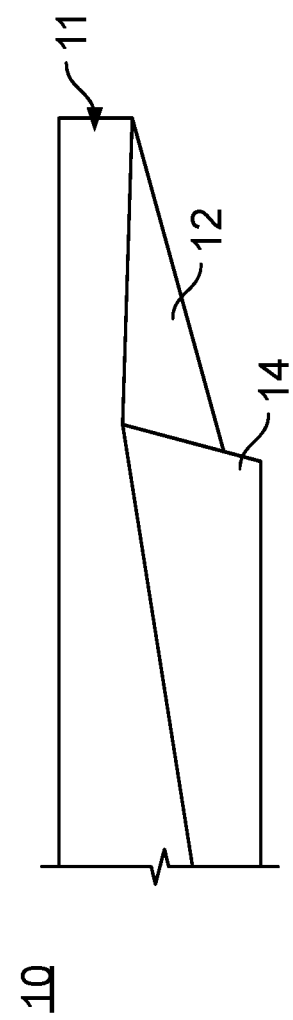

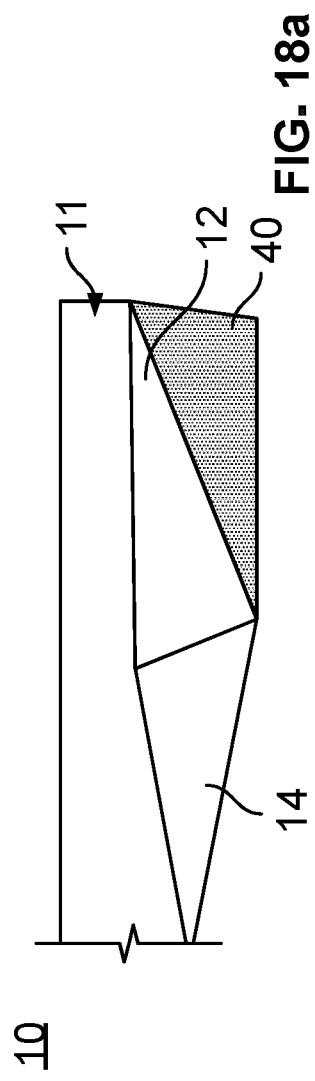
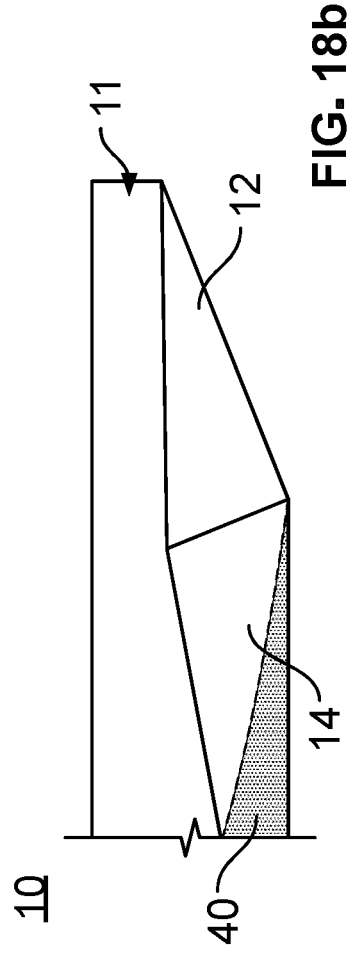
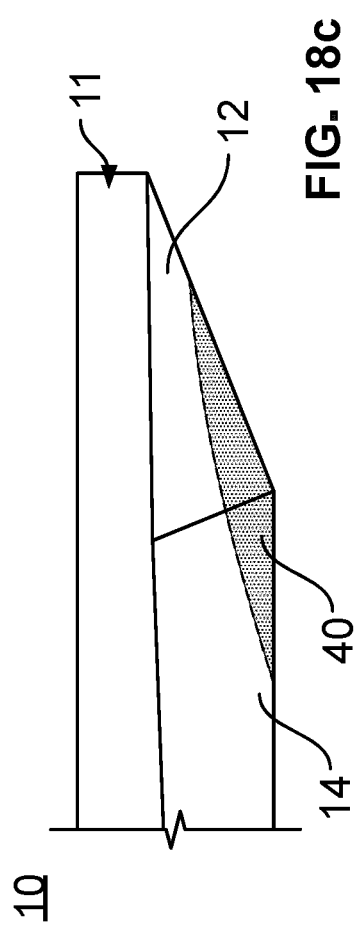

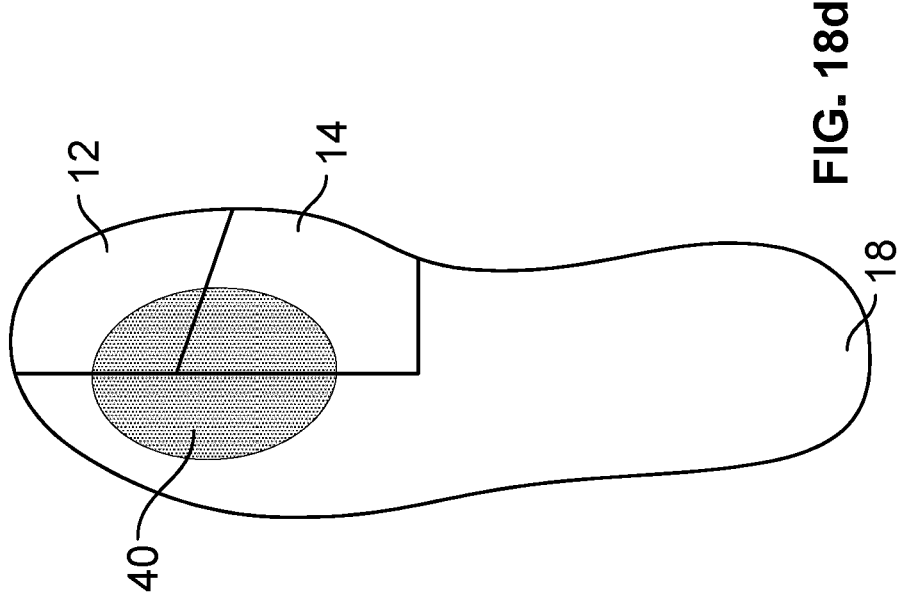

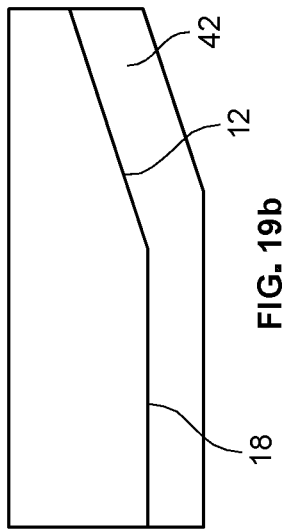
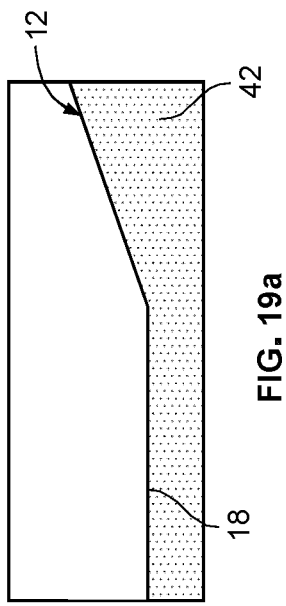

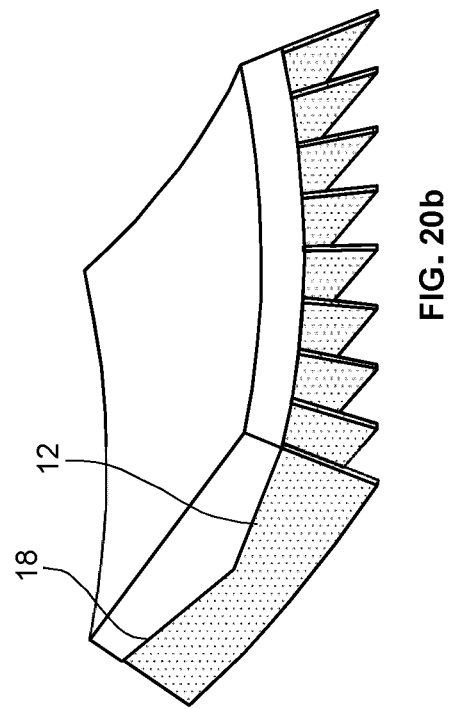
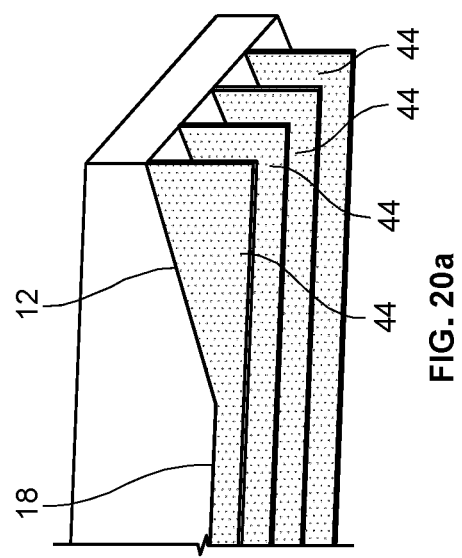

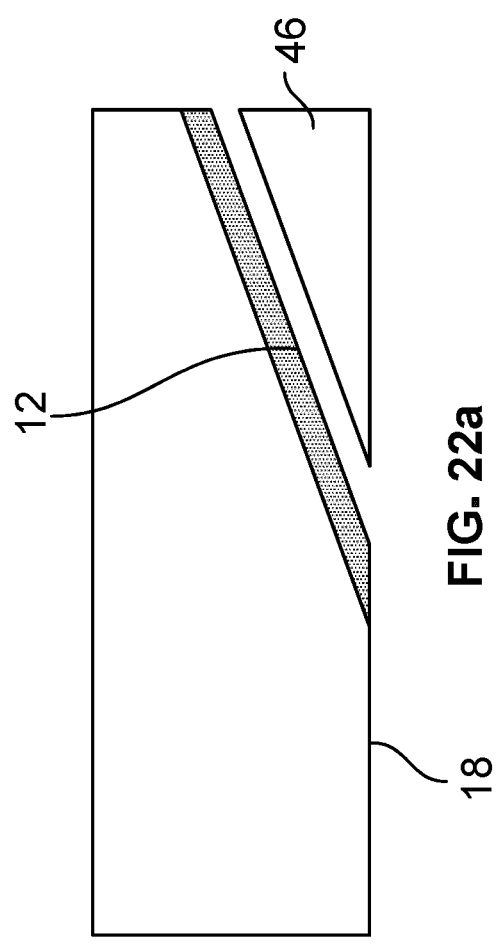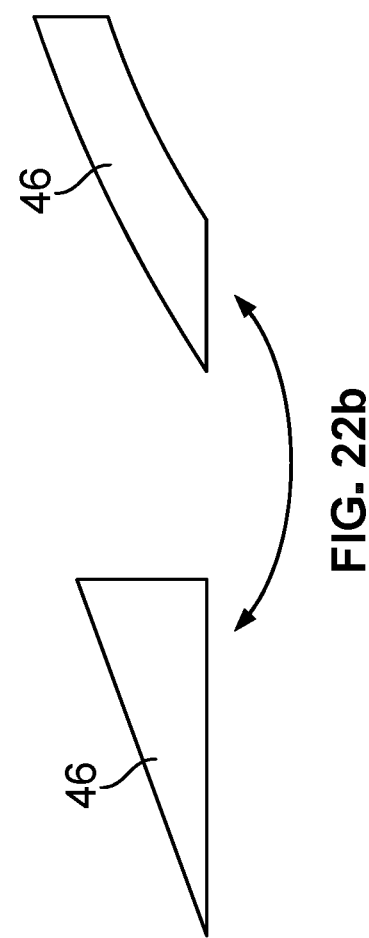

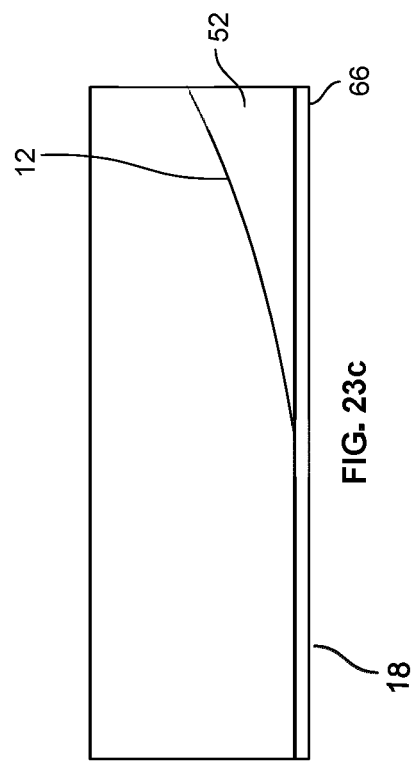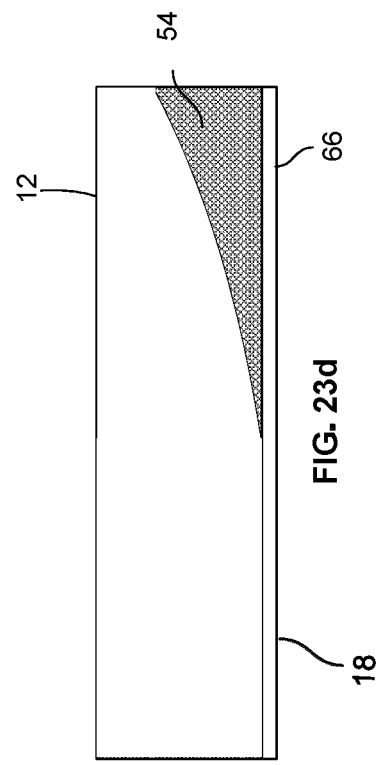

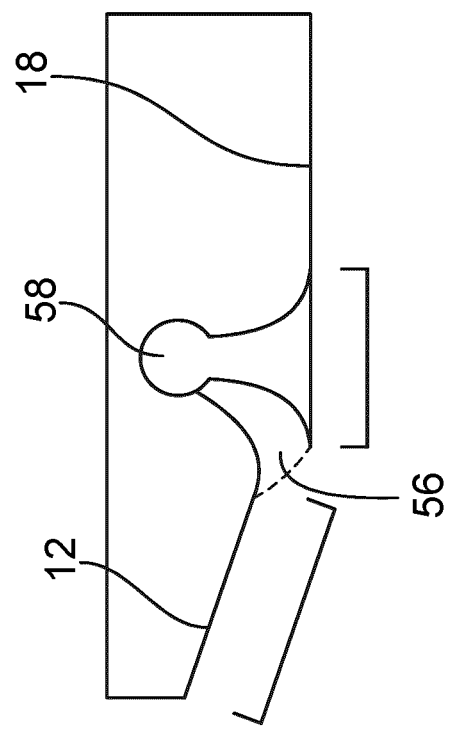
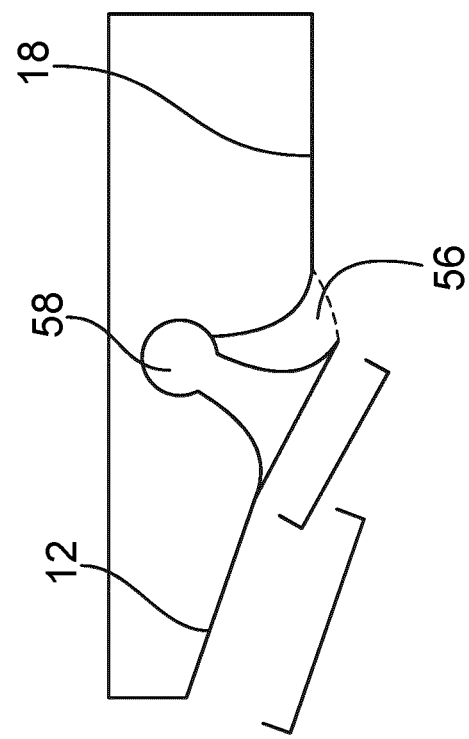

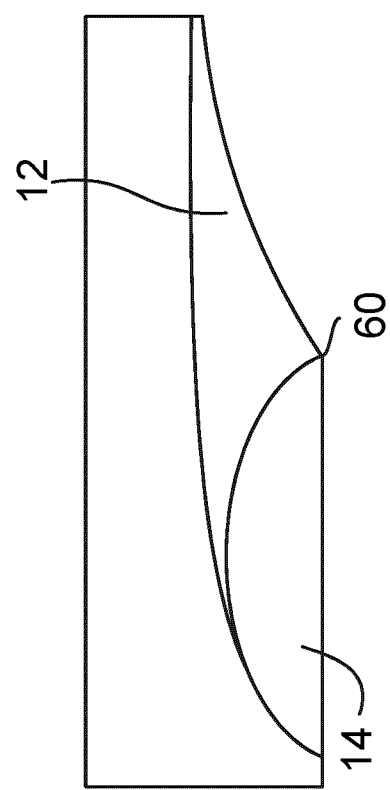

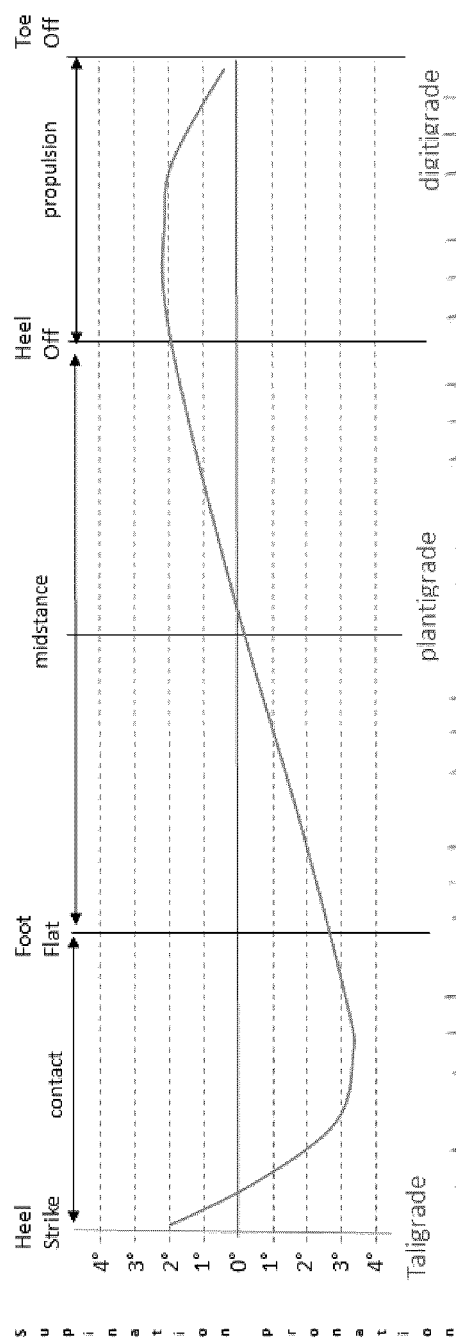
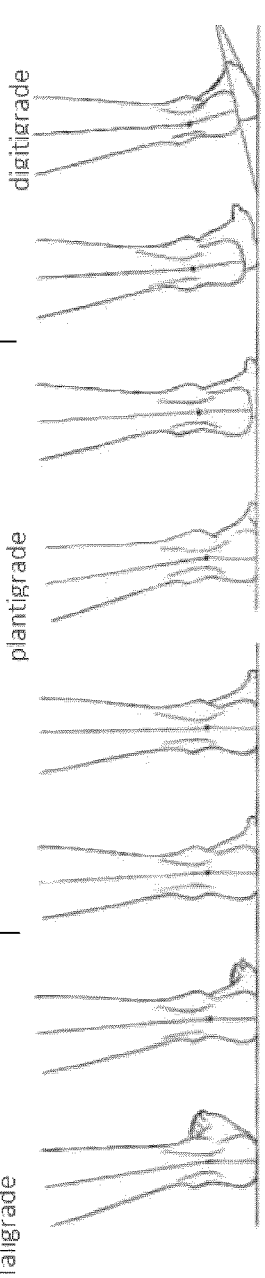
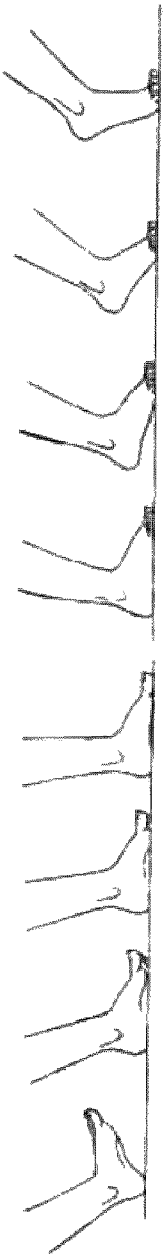
FIG. 27A
FIG. 27B
FIG. 27C
FIG. 27D

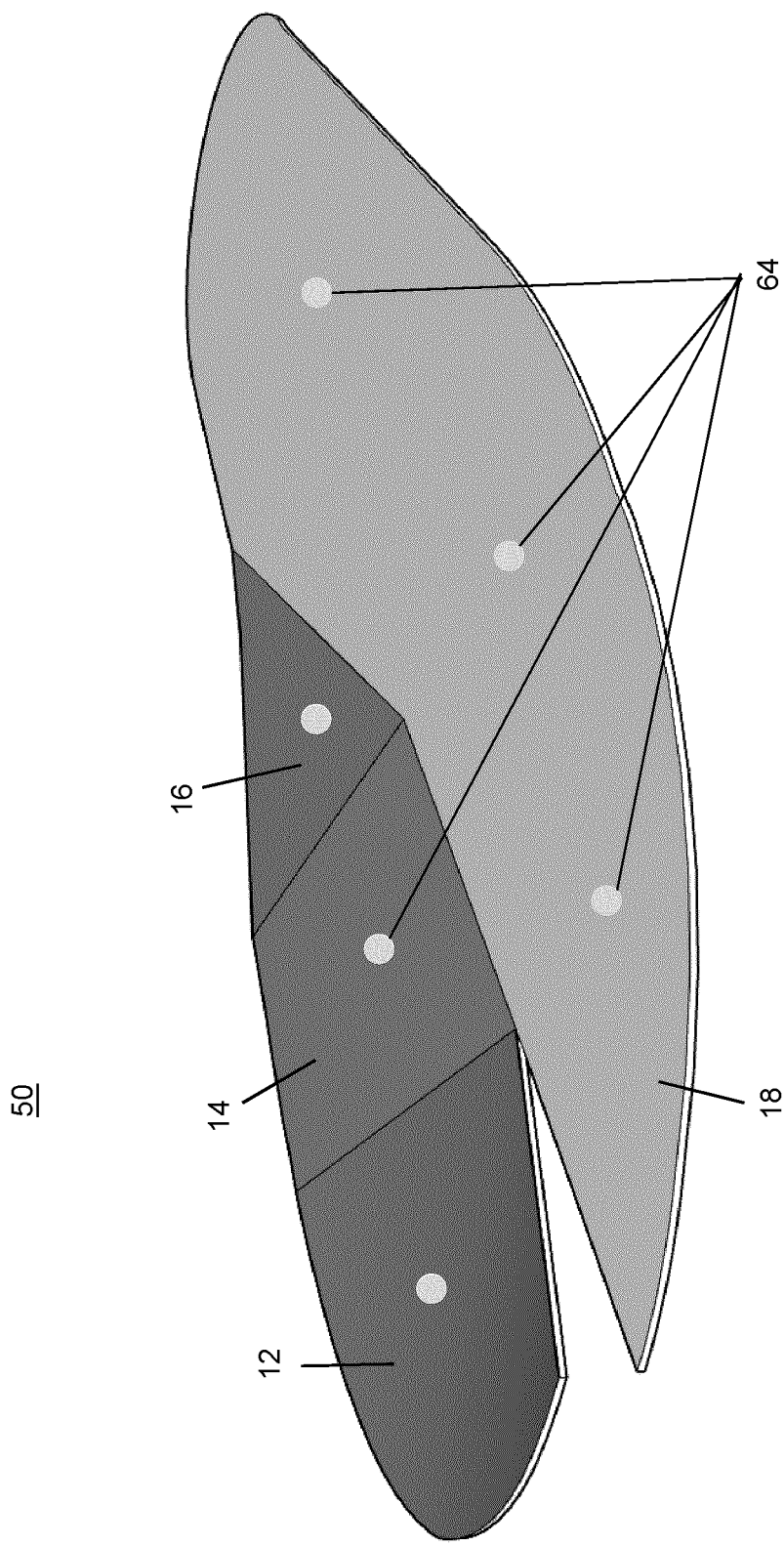

SOLE FOR FOOTWEAR WITH POSITIONING FACES

CROSS-REFERENCE TO RELATED APPLICATIONS

The present application is a continuation of PCT Application No. PCT/CA2019/050788 filed Jun. 6, 2019, which claims priority to U.S. Provisional Application No. 62/681,210 filed Jun. 6, 2018, the entireties of which are both incorporated herein by reference.

TECHNICAL FIELD

The following relates to a design for a sole for footwear.

BACKGROUND

Footwear such as shoes generally include a sole that is positioned at the bottom of the footwear, in contact with the ground. When the footwear is worn, the sole supports a wearer's foot some distance from the ground, and may also provide traction, cushioning, comfort, and other benefits to the wearer.

Soles can be constructed from a single layer of a single material, or multiple layers of one or more materials. A sole constructed of multiple layers typically comprises two or more of an insole, a midsole, and an outsole. The insole is the top layer of the sole, which sits beneath the wearer's foot. The outsole is the bottom layer of the sole, directly contacting the ground. The midsole is a layer between the outsole and the insole, which is typically provided for shock absorption.

Individuals may perform a variety of dynamic actions while wearing footwear, particularly athletic footwear, including running, jumping, side-stepping, pivoting, and making sudden changes of speed. Wearers often perform a variety of actions, and are required to shift their weight onto different parts of their feet such as their big toe, the ball of their foot, and their heel. It is less common for wearers to equally distribute their weight over their entire foot when performing such actions. For example, jumping vertically requires an individual to push off with the ball of their foot and their big toe, while landing from a horizontal jump requires an individual to contact the ground with their heel first. Many athletic actions, such as jumping forwards, jumping sideways and making quick lateral movements, require the wearer to shift their weight onto the ball of their foot.

Although a wearer may preferentially use specific parts of their feet for specific actions, the outsoles of footwear have traditionally been appreciably planar, causing several issues to arise. The repeated angling of a wearer's foot, such when shifting their weight onto the ball of their foot, may cause the sole of the footwear to repeatedly bend as one part of the sole is lifted while another part of the sole maintains contact with the ground. Such repeated bending may cause the sole to wear out, thus decreasing the lifespan of the shoe.

Another issue is that an individual wearing a shoe with a flat sole only achieves stable contact with the ground in one orientation; when the wearer's foot is flat against the ground. This causes a risk of injuries to joints such as the ankle and knee when a wearer shifts their weight, for example onto the ball of their foot. In one case, a wearer contacting the ground with a flat foot may quickly move or accelerate laterally. If their foot is unable to rotate while doing so, the wearer's ankle may become improperly pronated or oversupinated (FIG. 1), increasing the risk of injury to the ankle. In another case, a wearer contacting the ground with only the inside part of their foot is in an unstable position and may unexpectedly flatten their foot due to the instability of their stance, causing oversupination of their ankle and risk of an ankle sprain or other injury. Such cases may occur if the wearer attempts to rapidly accelerate or decelerate laterally.

Flat soled shoes may also increase a wearer's risk of injury when moving laterally by not encouraging alignment of the joints in the lower body, including the ankle, knee, and hip. Improper rotation of an ankle, knee, or hip when rapidly laterally accelerating or decelerating may cause a torn ACL, sprained ankle, or other injuries.

Shoes with flat soles are also unable to effectively concentrate force exerted by the wearer through balls of their feet. In addition, shoes with flat soles do not position the wearer in an athletic stance with their weight above the balls of the feet, such that they are better positioned to move quickly or change direction.

It is an object of the following to address at least one of the above-noted disadvantages.

SUMMARY

In one aspect, there is provided a sole for footwear, the sole comprising a bottom surface, the bottom surface comprising: a primary surface and one or more positioning face, wherein: the one or more positioning faces are at an angle to the primary surface; engaging a ground with the primary surface causes the footwear to provide a natural stance; and engaging the ground with the one or more positioning faces causes the footwear to provide one or more athletic stances.

In another aspect, there is provided a method of fixing defects in the natural gait of a user by creating a customized sole with positioning faces to compensate for, and fix problems related to supination and pronation of ankles. The customized sole can be created using various features as required by the results of the gait analysis. The features used to create the customized sole are described herein as alternative embodiments of the sole. The features can be used alone, or in combination to create a fully customized sole with positioning faces.

BRIEF DESCRIPTION OF THE DRAWINGS

Embodiments will now be described with reference to the appended drawings wherein:

FIG. 1a-1c illustrate the effect of lateral movement when using flat-soled shoes as known in the art;

FIG. 5 is a front view of the sole shown in FIG. 2, shown with a wearer;

FIG. 6 is a perspective view of the sole shown in FIG. 5 engaging the ground with angled positioning faces;

FIG. 7 is a rear perspective view of the sole shown in FIG. 6;

FIG. 9(a) is a plan view of another example of a sole with angled positioning faces;

FIG. 9(b) is a side view of the sole shown in FIG. 9(a);

FIGS. 12(a) to 12(j) are side views of variations of angled positioning faces.

FIGS. 17a and 17b show a medial view of an alternative embodiment of the sole wherein one positioning face is at a different height from the ground than the other positioning face;

FIGS. 18a-18c show medial views of an alternative embodiment of the sole with cushioning;

FIG. 18d shows a bottom view of the cushioned sole of FIG. 18c.

FIGS. 19a and 19b show a cross sectional view of embodiments of the sole with treads attached to the bottom of the sole.

FIGS. 20a and 20b show a perspective view of embodiments of the sole with flexible grooves attached to the bottom of the sole.

FIG. 21b is a bottom perspective view of the embodiment shown in FIG. 21a.

FIG. 22a is a cross sectional view of an embodiment of the sole showing a removable positioning face member.

FIG. 22b is a cross-sectional view of the removable positioning face member.

FIG. 23c shows a partial cross-sectional view of the sole with an air pocket.

FIG. 23d shows a partial cross-sectional view of the sole with a 3D printed structure.

FIGS. 24a-24b show front cross-sectional views of the sole with a lever mechanism.

FIG. 25 shows a partial medial view of the sole with a wedge mechanism.

FIG. 27a-27d shows a typical gait chart of a person.

FIG. 38 is a top perspective view of the plate in FIG. 37.

DETAILED DESCRIPTION

As discussed above, an individual wearing a shoe having a flat sole may experience one of several issues. FIG. 1(a) illustrates a foot 20 supported by a flat sole 30 of a shoe (not shown). An ankle 26 connecting the foot 20 to a lower leg 33 is in a neutral position, wherein the foot 20 and lower leg 33 are rotationally aligned resulting in minimal strain on the ankle 26.

Figure 1D:
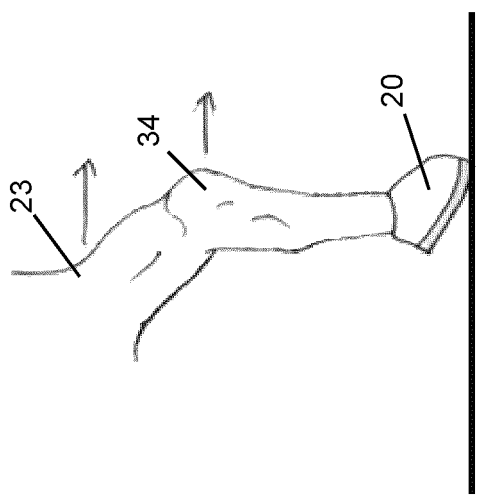
FIG. 1d illustrates the effect of lateral movement when using flat-soled shoes as known in the art.

A shoe with a flat sole only achieves stable contact with the ground when the entire bottom surface of the sole 30 is flat against the ground. When an individual wearing such a shoe makes sudden changes in lateral movement, for example stopping, accelerating, or making quick directional changes, the individual may thus experience a tendency to land with their sole 30 flat against the ground. As the individual performing such sudden changes in lateral movement often places their foot 20 away from their center of gravity, landing with their sole flat against the ground can result in improper pronation or oversupination of the ankle 26. If the foot 20 is a left foot, FIG. 1(b) illustrates inversion or supination of the ankle 26 and FIG. 1(c) illustrates eversion or pronation of the ankle 26. In addition, the individual's knee and hip may not be aligned with the force they are exerting on the ground to perform the sudden change in lateral movement. Thus, as illustrated in FIG. 1(d) the individual's momentum may cause the knee 34 and/or hip 32 to abduct outward, creating a risk of joint injury.

Figure 1E:
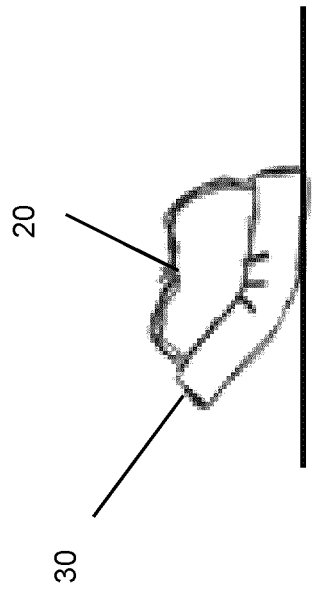
FIG. 1e illustrates the effect of pushing when using flat-soled shoes as known in the art.

If the individual wearing a shoe with a flat sole 30 lands on and launches from the ball of their foot 24 as shown in FIG. 1(e), the flat sole 30 may bend. This may result in bending of the foot 20 causing discomfort and/or accelerated wear on the flat sole 30.

To promote neutral ankle positioning when making lateral movements and/or to allow a wearer to easily shift their weight onto the balls of their feet; a shoe including a sole having positioning faces can be utilized, allowing a wearer of the shoe to stably engage the ground with their foot in multiple orientations. As described below, the positioning faces are at an angle to the remainder of the sole, allowing the wearer to position themselves by engaging the ground with different faces of the sole.

Figure 2:
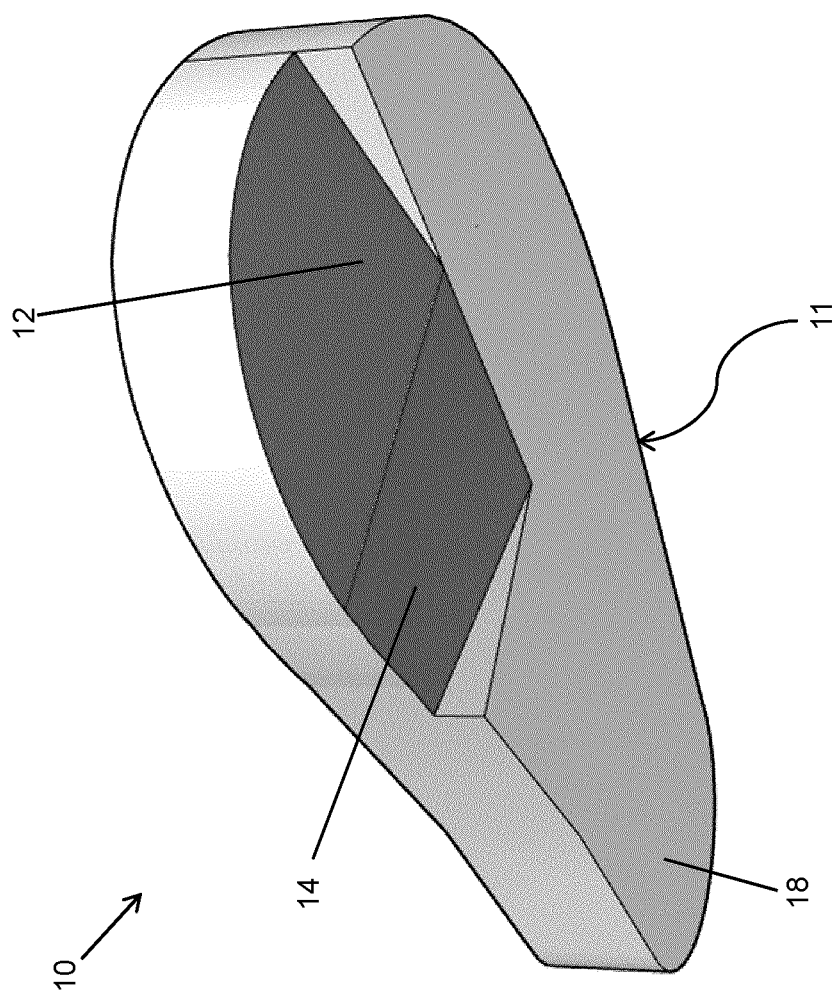
FIG. 2 is a bottom perspective view of a sole with angled positioning faces.

Turning now to the figures, FIG. 2 provides a perspective view of a sole 10 for footwear. It is herein understood that sole 10 refers to one of an outsole, midsole, or insole, or a combination thereof. For example, the sole 10 may be a midsole located between a separate outsole and an insole, or the sole 10 may be the completed assembly of an insole, midsole, and outsole. The sole 10 can be made from any material known in the art, for example rubber, foam, leather, or polyurethane. The interior or exterior of the sole 10 may also be provided with a support member, for example a rigid plate in the interior of the midsole to maintain its shape and prevent deformation. The sole 10 may be used in any type of footwear, for example athletic footwear such as a running shoe, trainer, basketball shoe, cleat, hiking boot, or ice skate.

The sole 10 has a bottom surface 11 located opposite a wearer's foot (not shown). The bottom surface 11 may be provided with a tread to engage an underlying surface such as a floor or the ground. The bottom surface 11 may alternatively be adapted to interface with another layer of the shoe, for example an enclosed layer of fluid such as air, gel or water underneath the sole to reduce the force of impact experienced by the wearer. The bottom surface 11 includes one or more positioning faces that are at an angle to a primary surface 18.

In the example shown in FIG. 2, the sole 10 for a left foot is provided with a first positioning face 12 and a second positioning face 14 on the bottom surface 11. The first positioning face 12 and the second positioning face 14 are angled upward, away from the bottom surface 11, as described in greater detail below. The primary surface 18, comprising the remainder of the bottom surface 11, is continuous and on a plane parallel to a top surface of the sole 10 and the ground. In this example, the primary surface 18 is illustrated as completely flat, however it is appreciated that the primary surface 18 may have texture such as a tread or varying curvature such as an arch support or a toe spring.

Figure 3:
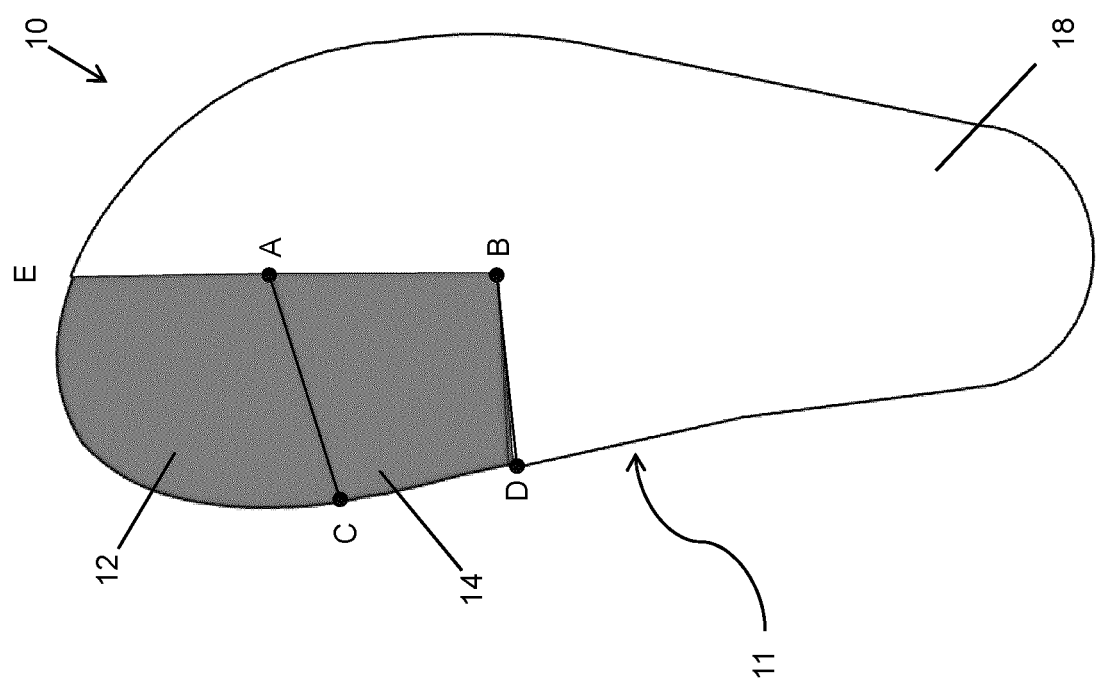
FIG. 3 is a bottom view of the sole shown in FIG. 2.

FIG. 3 illustrates the bottom surface 11 of the sole 10 illustrated in FIG. 2. The first positioning face 12 is located under the wearer's big toe 22 and the second positioning face 14 is located under the ball of the wearer's foot 24. First positioning face 12 and second positioning face 14 are defined by points A, B, C, D, and E, as described below. First positioning face 12 has vertices at points A, C, and E, and has a curved edge from point C to point E to match the contour of the sole 10. Second positioning face 14 has vertices at points A, B, C, and D. The positioning faces 12, 14 are illustrated as planar, however it should be appreciated that one or more of the positioning faces may be convex, concave, or otherwise non-planar.

Figure 4:
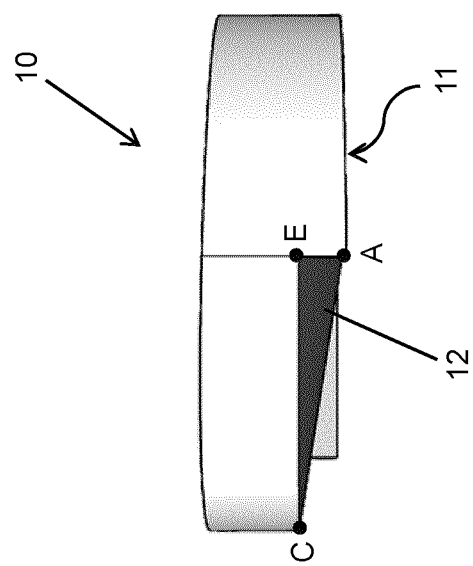
FIG. 4 is a front view of the sole shown in FIG. 2.

FIG. 4 shows a front view of the sole. It can be observed from FIG. 4 that, in this example, the thickness of the sole 10 along the edge from point C to point E is less than the thickness of the sole 10 at point A. The thickness gradient from point A to points C and E creates the first positioning face 12 that is angled upward and away from the bottom surface 11. Similarly, the thickness of the sole 10 at point D is less than the thickness at point B, such that the second positioning face 14 is angled upwardly and away from the bottom surface 11.

FIG. 5 shows a front view of a user's foot wearing the sole. FIG. 5 shows the sole 10 in isolation, supporting a foot 20 belonging to a wearer, for example as would normally be the case when the foot 20 is in a shoe (not shown for ease of illustration) that includes the sole 10. The points A, B, C, D, and E (FIG. 3) are located on the sole 10 such that the wearer's big toe 22 is partially or entirely located above the first positioning face 12, and the ball of the wearer's foot 24 is partially or entirely located above the second positioning face 14. The points may be positioned such that more than one of the wearer's toes, such as the big toe 22 and a second toe, are located above the first positioning face 12. The positioning faces 12 and 14 may be of any size, and larger positioning faces may result in greater stability when engaging the ground with the positioning faces, as described in greater detail below. For example, the points A, B, C, D, and E may be placed such that the wearer's big toe 22 and second toe are above the first positioning face 12 and the second positioning face extends beyond the ball of the wearer's foot 24.

FIG. 5 shows the wearer in a natural stance. The primary surface 18 engages the ground and the foot 20 is oriented such that the ankle 26 is in a neutral position. A natural stance may result from the wearer standing straight with their foot 20 directly underneath their body.

It can be seen from FIG. 6 that the sole 10 allows the wearer to engage the ground with first positioning face 12 and/or second positioning face 14 in an athletic stance, as described below. In this example, the wearer in the athletic stance maintains a neutral ankle 26. That is, the ankle 26 is not supinated or pronated. The wearer may switch between the natural stance and the athletic stance by pivoting the sole 10 around the line defined by points E, A, D and B (FIG. 3), thus switching between engaging the ground with the primary surface 18 and engaging the ground with the first positioning face 12 and/or the second positioning face 14. Such switching may be initiated by the wearer shifting their weight forward, so their center of gravity is over the front portion of their foot. The wearer may also lift their foot 20 and place it down in the athletic stance such that the angled positioning face 12, 14 engage the ground. The wearer may still take a natural stance when performing certain actions, and switch to the athletic stance when performing actions that require them to engage the ground with the ball of their foot 24. The wearer is not always forced into an athletic stance, which may cause strain.

FIG. 7 shows a back view of a user's foot wearing the sole. FIG. 7 illustrates an example of the sole 10 engaging the ground with a lower leg 33 belonging to the wearer at an angle to the ground. The wearer may engage the ground with the lower leg 33 angled when the foot 20 is positioned laterally beyond (outside) the hip, for example when running sideways or rapidly accelerating or decelerating laterally. An angled lower leg 33 may increase the risk of injury if the foot 20 flatly engages the ground, causing oversupination or improper pronation of the ankle 26.

The wearer may adjust their footing to apply pressure directly on the positioning faces 12 14, causing the primary surface 18 to be elevated from the ground. If the wearer stops applying pressure to the positioning faces 12 14, the heel 23 and/or the primary surface 18 will engage the ground and the positioning faces 12 14 will become elevated from the ground. The heel 23 and/or primary surface 18 may not always elevate from the ground. This could be due to localized pressure in the foot and/or soles while using the positioning faces, or due to the design and material of the sole or plate.

A wearer using sole 10 may engage the ground with the first positioning face 12 and/or the second positioning face 14 when their lower leg 33 is at an angle to the ground. By engaging the ground with angled positioning faces 12, 14, the foot 20 exerts force on the ground mainly with the big toe 22 and/or the ball 24. The primary surface 18 and/or the heel 23 are raised, causing the foot 20 to be oriented at an angle to the ground. In this example, the foot 20 is oriented such that it is aligned with the lower leg 33, allowing the ankle 26 to adopt a neutral position even though the lower leg 33 is at an angle to the ground.

The first positioning face 12 and second positioning face 14 provide platforms through which the big toe 22 and ball of the foot 24 can exert force more efficiently on the ground. The angled positioning faces 12, 14 provide additional stable orientations for the sole 10, resisting rocking or flattening of the sole 10 when the wearer assumes the athletic stance. That is, a wearer engaging the ground with the first positioning face 12 and/or the second positioning face 14 achieves stable contact with the ground, and may be less likely to rotate or flatten the foot 20 causing oversupination or improper pronation of the ankle 26.

As shown in FIGS. 6 and 7, engaging the ground with the first positioning face 12 and/or the second positioning face 14 allows the wearer to adopt the athletic stance. In the athletic stance, the sole 10 causes the wearer to shift their weight forward onto the ball of their foot 24 and/or their big toe 22, and/or lift their heel 23 off the ground. The shift of the wearer's weight onto the ball of their foot 24 may also cause the wearer to partially bend their knee (not shown). In the athletic stance, the wearer exerts force on the ground with the ball of their foot 24, allowing for faster, more explosive movements as the wearer can exert more force on the ground with the second positioning face 14. The wearer may be able to react and move faster if they are in the athletic stance instead of the natural stance. The athletic stance may also cause the wearer's knees to align with their ankles, providing greater stability and allowing the wearer to exert a larger force with their legs. Additionally, if the wearer is already in the athletic stance, they are not required to shift their weight forward onto the ball of their foot 24 to perform such movements.

Figure 8:
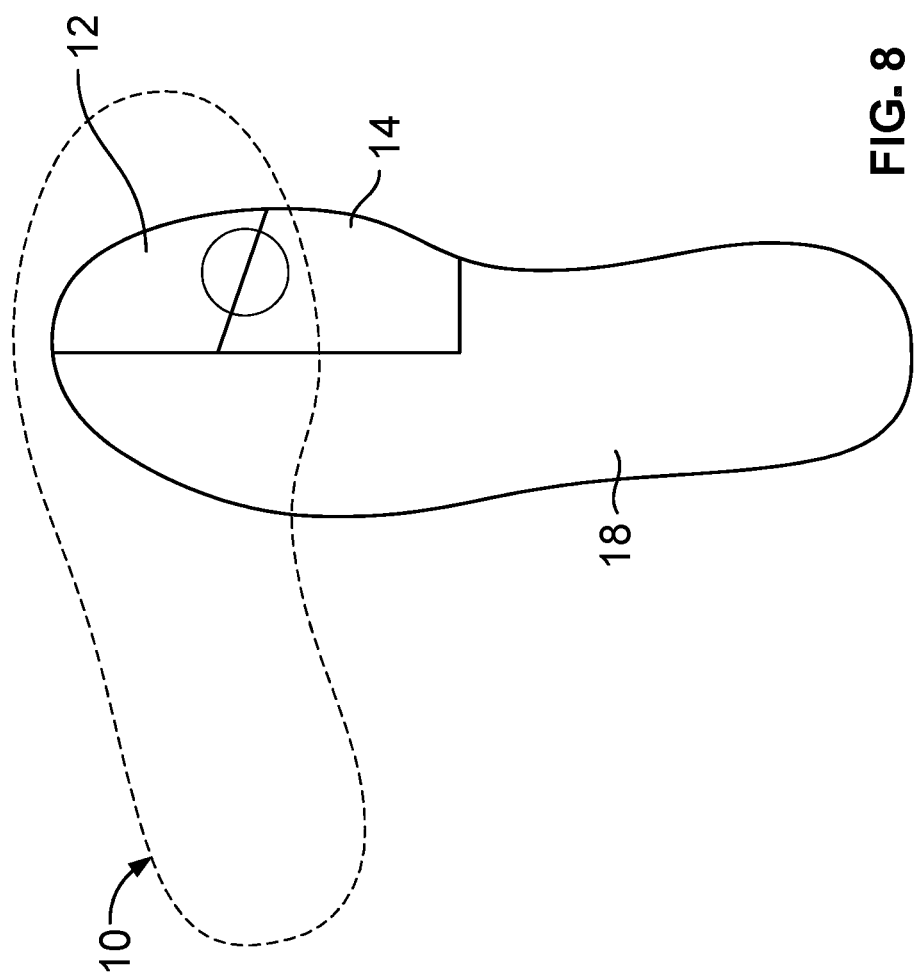
FIG. 8 is a bottom view of a pivoting sole.

The wearer may also pivot when engaging the ground when in the athletic stance. FIG. 8 illustrates a sole 10 engaging the ground with the angled positioning faces 12, 14 pivoting from an initial position represented by a dashed outline. Pivoting is performed most effectively when the wearer engages the ground only with the big toe 22 and ball of the foot 24, allowing faster rotation, more flexibility, and more freedom of foot position. By not engaging the ground with the entire sole 10, the decreased surface area contacting the ground reduces the traction, allowing the foot 20 to pivot with less torque. In addition, the rounded contour of the first positioning face 12 allows for the wearer to make directional changes more easily.

Another example of a sole for footwear provided with positioning faces is shown in FIGS. 9(a) and 9(b). The bottom surface 11 of a sole 10 for a right foot is provided in this example with a first positioning face 12, a second positioning face 14, and a third positioning face 16. The first positioning face 12 has vertices at the points A, C, and E, and has a curved edge from point C to point E to match the contour of the sole 10. The second positioning face 14 is has vertices at the points A, B, C, and D, and the third positioning face 16 has vertices at the points B, D, and F.

The points A, B, C, D, E, and F are located on the sole 10 such that a wearer's big toe 22 is partially or entirely located above the first positioning face 12, the ball of the wearer's foot 24 is partially or entirely located above the second positioning face 14, and the arch of the wearer's foot is partially or entirely located above the third positioning face 16. The heel of the wearer's foot 23 can also be partially or entirely located above the third positioning face 16. The points may be positioned such that more than one of the wearer's toes are located above the first positioning face 12. The points may also be positioned such that the ball of the wearer's foot 24 is only partially located above the second positioning face, or such that the ball of the foot 24 and a surrounding area of the wearer's foot 20 is located above the second positioning face.

The first positioning face 12, second positioning face 14, and third positioning face 16 are angled upward and away from the bottom surface 11. The primary surface 18, comprising the remainder of the bottom surface 11, is on a plane parallel to a top surface of the sole 10 and the ground. In this example, the primary surface 18 is illustrated as completely flat, however it is appreciated that the primary surface 18 may have texture such as a tread or varying thickness such as an arch support or a toe spring.

The wearer may engage the ground with the primary surface 18 in a natural stance or with one or more of the positioning faces 12, 14, 16 in an athletic stance, as described above. The third positioning face 16 increases the area of the sole 10 in contact with the ground when the wearer takes the athletic stance, providing the wearer increased balance and greater stability. The third positioning face 16, line defined by points E, A, F and B, may also allow the wearer to switch between the natural stance and the athletic stance with a smaller forward or backward shift of weight.

One or more of the first positioning face 12, second positioning face 14, and third positioning face 16 may be subdivided along the length, width, and/or height of the sole 11 into two or more subfaces. The subfaces may be at different angles to the bottom or edges of the sole 10, such that the wearer engages the ground with different subfaces by adjusting the orientation of the sole 10. It should be apparent that a sole with subdivided positioning faces provides the wearer with greater range, as multiple different foot orientations result in the wearer engaging the ground with one or more subfaces.

Figure 10:
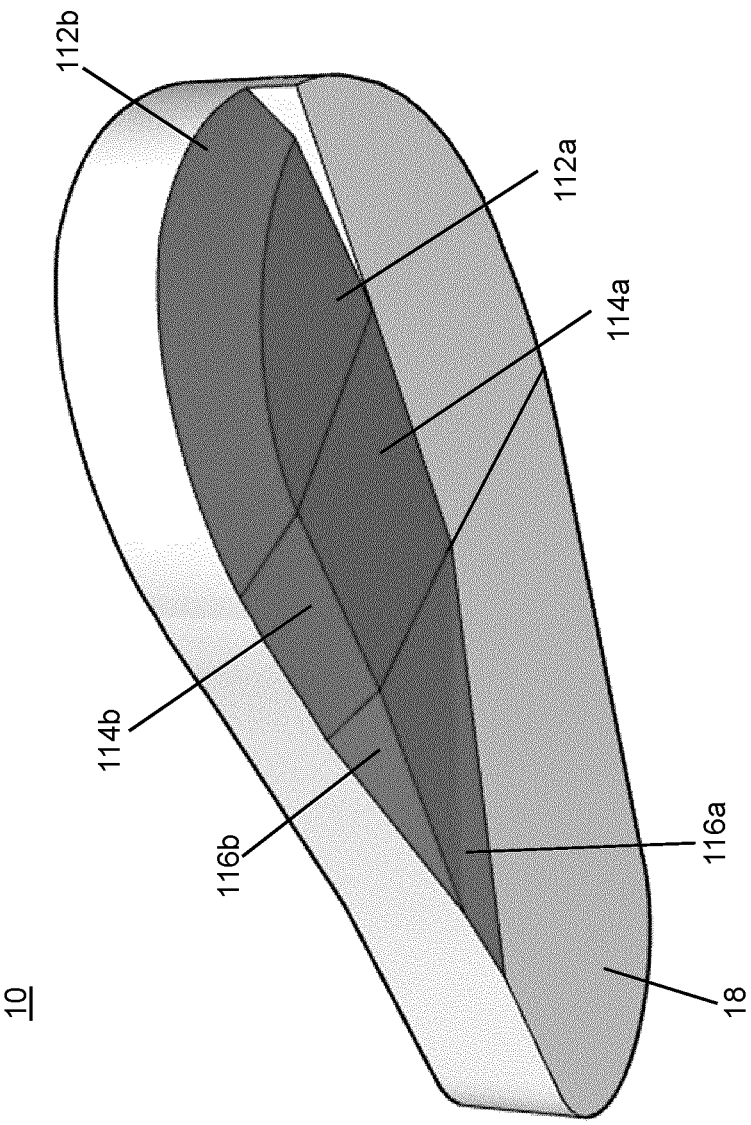
FIG. 10 is a perspective view of a sole with subdivided positioning faces.

FIG. 10 shows a first example of a sole 10 having three subdivided positioning faces, analogous to the sole illustrated in FIGS. 9(a) and 9(b) with like elements given like reference numerals preceded by a "1". The sole 10 is provided with a first positioning face 112, a second positioning face 114, and a third positioning face 116. The first positioning face 112 is subdivided into lower first positioning subface 112a and upper first positioning subface 112b, the second positioning face 114 is subdivided into lower second positioning subface 114a and upper second positioning subface 114b, and the third positioning face 116 is subdivided into lower third positioning subface 116a and upper third positioning subface 116b. The wearer of the sole 10 engages the ground with the primary surface 18 when in a natural stance. The wearer can engage the ground with the lower first positioning subface 112a, lower second positioning subface 114a, and lower third positioning subface 116a by shifting their weight forward and inward to take a first athletic stance, as described above. The wearer may shift their weight further forward or inward to a second athletic stance to engage the ground with one or more of the upper first positioning subface 112b, upper second positioning subface 114b, and upper third positioning subface 116b. The upper positioning subfaces 112b, 114b, 116b may also be adapted for aesthetics, providing a gradual transition between the appreciably horizontal lower positioning subfaces 112a, 114a, 116a and the appreciably vertical side walls of the sole 10.

Figure 11:
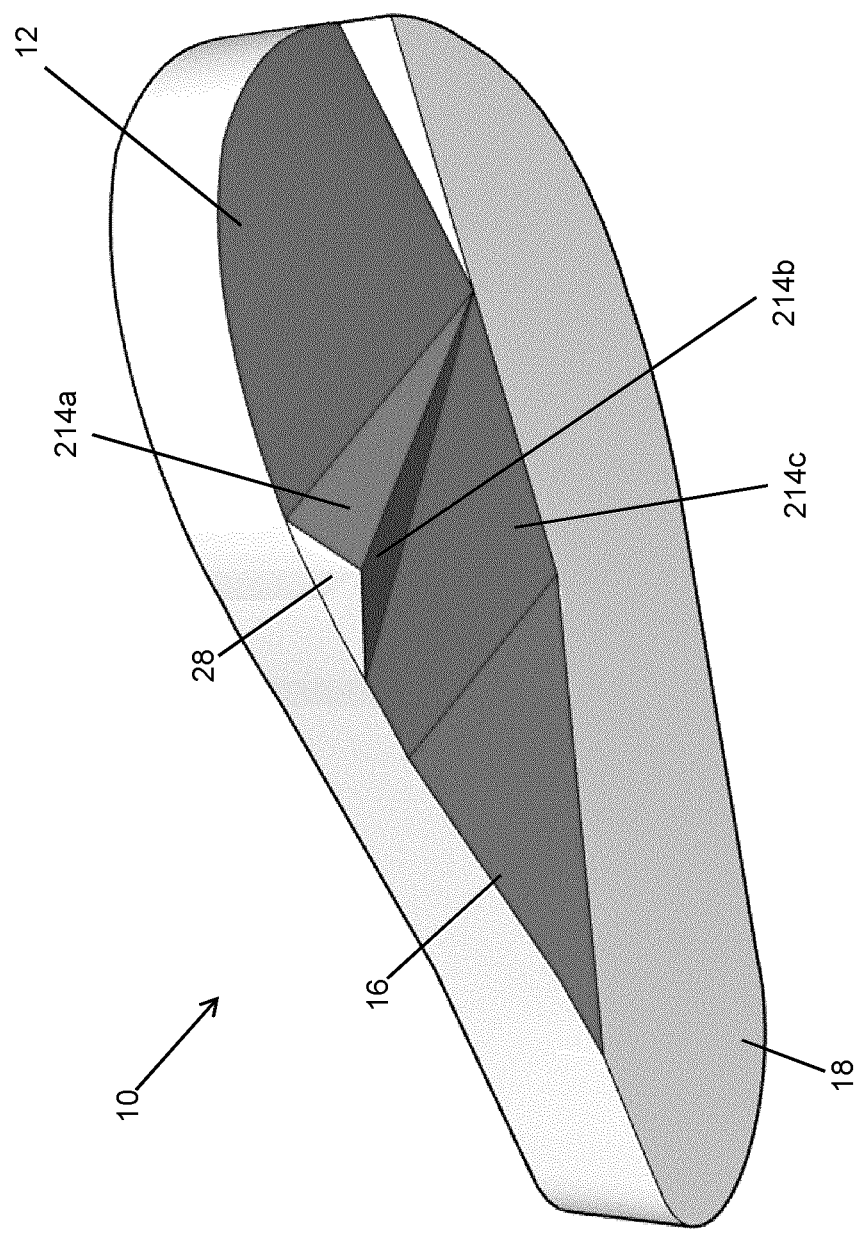
FIG. 11 is a perspective view of another example of a sole with subdivided positioning faces.

FIG. 11 shows a second example of a sole 10 having one positioning face subdivided twice, analogous to the sole illustrated in FIGS. 9(a) and 9(b) with like elements given like reference numerals preceded by a "2". The sole 10 is provided with first positioning face 12, a second positioning face 214, and third positioning face 16. The second positioning face 214 is subdivided into front second positioning subface 214a, middle second positioning subface 214b, and rear second positioning subface 214c. Subfaces 214a and 214b form a wedge 28 having an apex towards the bottom surface 11. The wedge 28 allows the wearer to shift their weight forward and engage the ground with the third positioning face 16, rear second positioning subface 214c, and middle second positioning subface 214b in a first athletic stance; and the wearer may shift their weight further forward to engage the ground with the front second positioning subface 214a and first positioning face 12 in a second athletic stance.

Two examples of soles having subdivided positioning faces are described above, however it should be appreciated that the positioning faces may be subdivided in any other way.

FIGS. 12(a) and 12(b) show a side view of a preferred implementation of the angled positioning faces 12, 14. The third positioning face 16 is not shown, and it is understood that the implementation of the positioning faces 12, 14 on the sole 10 may optionally include additional positioning faces such as the third positioning face 16. Points A and B are at the same height, or level, and points C and D are at the same height. Points A and B are level with the primary surface 18. The second positioning face 14 is planar, and has a uniform upslope from the edge between points A and B to the edge between points C and D. In this embodiment, the first positioning face 12 curves along the contour of the sole 10 from point C to point E. Optionally, the first positioning face 12 does not need to follow the edges of the sole.

FIGS. 12(c) through 12(j) illustrate side views of other examples of implementations of the first positioning face 12 and second positioning face 14, in isolation. The third positioning face 16 is not shown, and it is understood that the implementation of the positioning faces 12, 14 on the sole 10 may optionally include additional positioning faces such as the third positioning face 16. The terms "lower" or "towards the ground", and "higher" or "away from the ground" may be used in the description. It is herein understood that these groups of terms describe directions along the thickness of the sole meaning "towards the bottom surface of the sole" and "away from the bottom surface of the sole" respectively. The terms "forward" and "backward" may be used herein, and it is understood that these terms describe directions along the length of the foot meaning "towards the toes" and "towards the heel" respectively.

In the example illustrated in FIG. 12(c), the points A, C, D, and E are in the same position as in the preferred implementation. Point B is raised away from the ground, such that it is higher than point A. The higher placement of point B allows this example to be incorporated into shoe designs comprising a raised midsection or arch, and support the arch of the foot. This example causes the wearer to lean backwards slightly to stabilize the heel portion of their foot 23 and can be used to help the wearer balance.

In the example illustrated in FIG. 12(d), the points B, C, D, and E are in the same position as in the preferred implementation. Point A is raised away from the ground, such that it is higher than point B. The higher placement of point A causes the wearer to shift their weight further forwards towards their toes. In addition, the sole 10 provides the wearer with two athletic stances; the user can engage the ground with only the first positioning face 12 or only the second positioning face 14, and can switch between the two. This stance helps the user propel their foot forward.

In the example illustrated in FIG. 12(e), the points A, B, C, and D are in the same position as in the preferred implementation. Point E is raised away from the ground, such that it is higher than points C and D. The higher placement of point E creates a steeper gradient of the first positioning face 12 between point A and point E, causing the wearer's weight to be further forward when they are engaging the ground with the first positioning surface 12. The steeper gradient of the first positioning face 12 can be used to improve the wearer's ability to push off with their big toe 22 when engaging the ground with the first positioning face 12.

In the example illustrated in FIG. 12(f), the points A, B, C, and D are in the same position as in the preferred implementation. Point E is lowered towards the ground, such that it is lower than points C and D. The lower placement of point E creates a more gradual gradient of the first positioning face 12 between point A and point E. The more gradual gradient of the first positioning face 12 can be used to allow for the wearer to make more controlled movements, and can provide a more stable surface when the wearer is in the athletic stance.

In the example illustrated in FIG. 12(g), the points A, B, D, and E are in the same position as in the preferred implementation. Point C is raised away from the ground, such that it is higher than points D and E. The higher placement of point C creates a gradient of second positioning face 14 between points D and C. This example can be used to allow the wearer to engage the ground preferentially with the second positioning face 14, and raise the primary surface 18 further off the ground as their weight is shifted further forward towards the ball of their foot 24.

In the example illustrated in FIG. 12(h), the points A, B, D, and E are in the same position as in the preferred implementation. Point C is lowered towards the ground, such that it is lower than points D and E. The lower placement of point C can be used to provide the wearer more balance and stability when they are engaging the ground with the second positioning face 14, as their weight will not be as far forward. The first positioning face 12 has a steeper gradient, causing the wearer's weight to be further forward when they are engaging the ground with the first positioning face 12. The wearer can switch between two athletic stances, engaging the ground with only one of first positioning face 12 or second positioning face 14 by adjusting their weight forward or backward.

In the example illustrated in FIG. 12(i), the points A, B, and D are in the same position as in the preferred implementation. Points C and E are raised away from the ground, such that they are higher than point D. The higher placement of point C can be used to create a gradient of second positioning face 14 between points D and C, causing the wearer to shift their weight further forward when engaging the ground with second positioning face 14. The higher placement of point E can be used to create a steeper gradient of the first positioning face 12 between point A and point E, causing the wearer's weight to be further forward when they are engaging the ground with the first positioning surface 12. The steeper gradient of the first positioning face 12 can be used to improve the wearer's ability to push off with their big toe 22 when in the athletic stance.

In the example illustrated in FIG. 12(j), the points A, B, and D are in the same position as in the preferred implementation. Points C and E are lowered towards the ground, such that they are lower than point D. This example can be used to cause the wearer's weight to be further back away from their toes when in the athletic stance.

FIG. 13(a) shows a bottom view of the preferred implementation of angled positioning faces 12, 14, as illustrated in FIG. 3, in isolation. The third positioning face 16 is not shown, and it is understood that the implementation of the positioning faces 12, 14 on the sole 10 may optionally include additional positioning faces such as the third positioning face 16. As described above, points A, B, C, D and E are located on the sole 10 such that the wearer's big toe 22 is partially or entirely located above the first positioning face 12, and the ball of the wearer's foot 24 is partially or entirely located above the second positioning face 14. The points may be positioned such that more than one of the wearer's toes are located above the first positioning face 12. The points may also be positioned such that the ball of the wearer's foot 24 is only partially located above the second positioning face, or such that the ball 24 and a surrounding area of the wearer's foot 20 is located above the second positioning face.

In the preferred implementation, the first positioning face 12 is curved from point C to point E to follow the contour of the sole 10 and allow the wearer to pivot. Point C is closer to the back of the foot than point A to create a larger surface for the big toe 22 to push off with when the wearer is engaging the ground with the first positioning face 12. The second positioning face 14 has a uniform gradient from the edge between points A and B and the edge between points C and D, allowing the wearer to effectively exert force to change directions when engaging the ground with the second positioning face 14.

FIGS. 13(*b*) through 13(*t*) and 14(*a*) through 14(*p*) illustrate bottom views of other examples of implementations of the first positioning face 12 and second positioning face 14, in isolation. The third positioning face 16 is not shown, and it is understood that the implementation of the positioning faces 12, 14 on the sole 10 may optionally include additional positioning faces such as the third positioning face 16. The terms "medial" and "lateral" are used herein, and it is understood that these terms describe directions along the width of the foot meaning "towards the center of the body" and "away from the center of the body" respectively.

In the example illustrated in FIG. 13(*b*), the points C, D, and E are in the same position as in the preferred implementation. Points A and B is moved laterally. The placement of points A and B widens the second positioning face 14 and can be used to provide a larger surface for the ball of the foot 24 to balance on and therefore greater stability when the wearer is in the athletic stance. In addition, the adjustment of point A widens the first positioning face 12, creating a more gradual gradient and providing more area for a second toe belonging to the wearer.

In the example illustrated in FIG. 13(*c*), the points B, C, D, and E are in the same position as in the preferred implementation, with point A moved laterally. The placement of point A widens the front part of second positioning face 14, and can be used to cause the wearer to shift their weight slightly forward when in the athletic stance. In addition, the adjustment of point A widens the first positioning face 12, creating a more gradual gradient and providing more area for a second toe belonging to the wearer.

In the example illustrated in FIG. 13(*d*), the points C, D, and E are in the same position as in the preferred implementation, with points A and B moved medially. The adjustment of points A and B decrease the size of second positioning face 14, decreasing the stability of the wearer in the athletic stance and thus encouraging the wearer to only adopt the athletic stance to make fast, explosive movements. Additionally, the size of the primary surface 18 is increased, such that the sole can engage the ground with a larger surface when the wearer is in the natural position. The size of the first positioning face 12 is slightly decreased, and can allow the big toe 22 to more effectively transfer force when the wearer is in the athletic stance.

In the example illustrated in FIG. 13(*e*), the points B, C, D, and E are in the same position as in the preferred implementation, with points A moved medially. The adjustment of point A creates a steeper gradient of the first positioning face 12. Additionally, the size of the first positioning face 12 is slightly decreased, and can allow the big toe 22 to more effectively transfer force when the wearer is in an athletic stance. The second positioning face 14 has a slightly backward gradient. The wearer can switch between two athletic stances, engaging the ground with only one of first positioning face 12 or second positioning face 14 by shifting their weight forward or backward.

In the example illustrated in FIG. 13(*f*), the points A, C, D, and E are in the same position as in the preferred implementation, with point B moved laterally. The adjustment of point B increases the area of the second positioning face 14, and can provide greater stability when the wearer is in the athletic stance. The increased area can additionally improve the transition from engaging the ground with the primary surface 18 to engaging the ground with the second positioning face 14.

In the example illustrated in FIG. 13(*g*), the points A, C, D, and E are in the same position as in the preferred implementation, with point B moved medially. The adjustment of point B reduces the area of the second positioning face 14 and can be used to cause the wearer to shift their weight forward.

In the example illustrated in FIG. 13(*h*), the points A, and C are in the same position as in the preferred implementation, with point E moved laterally and points B and D moved forward. The adjustment of points B and D shortens the second positioning face 14, decreasing stability in the ball of the foot 24 when the wearer is in the athletic stance but can be used to allow the wearer to perform faster forward motions. The adjustment of point E increases the area of the first positioning face 12, creating a larger surface for the wearer to pivot on and can allow the wearer to transfer force through multiple toes when in the athletic stance.

In the example illustrated in FIG. 13(*i*), the points A, C, and D are in the same position as in the preferred implementation, with point B moved medially and point E moved laterally. The adjustment of point B reduces the area of the second positioning face 14 and causes the wearer to shift their weight forward. The adjustment of point E increases the area of the first positioning face 12, creating a larger surface for the wearer to pivot on and can be used to allow the wearer to transfer force through multiple toes when in the athletic stance.

In the example illustrated in FIG. 13(*j*), points C, D, and E are in the same position as in the preferred implementation, with point A moved laterally and point B moved laterally further than point A. The second positioning face 14 is increased in area, with the back edge between points B and D widened more than the front edge between points A and C to cause the wearer to shift their weight slightly forward and provide more stability when in the athletic stance. The adjustment of point additionally A widens the first positioning face 12, and can be used to create a more gradual gradient and providing more area for the wearer's second toe. This example may be used to assist the user in moving sideways, backwards, or diagonally.

In the example illustrated in FIG. 13(*k*), the points A, B, C, and E are in the same position as in the preferred implementation, with point D moved backward. The adjustment of point D increases the area of the second positioning face 14, and can be used to provide greater stability when the wearer is in the athletic stance. Additionally, the adjustment of point D can allow the wearer to shift sideways quickly.

In the example illustrated in FIG. 13(*l*), the points B, D, and E are in the same position as in the preferred implementation, with points A and C moved backward. The adjustment of points A and C shortens the second positioning face 14, while lengthening the first positioning face 12. This can be used to decrease stability when the wearer is in the athletic stance, and cause the wearer to shift their weight forward onto their toes.

In the example illustrated in FIG. 13(*m*), the points D and E are in the same position as in the preferred implementation, with point A moved medially and backward, point B moved medially, and point C moved backward. The adjustment of points A, B, and C decreases the area of the second positioning face 14, and can be used to reduce the frequency that the wearer engages the ground with the second positioning face 14 in an athletic stance. The adjustment of points A and C increase the length of the first positioning face 12 while slightly decreasing the width, and can allow the wearer to more explosively exert force through their big toe 22 when in the athletic stance.

In the example illustrated in FIG. 13(n), the points E and D are in the same position as in the preferred implementation, with point A moved laterally and backward, point B moved laterally, and point C moved backward. The adjustment increases the width of the second positioning face 14, and can be used to allow the wearer to shift their weight to more easily switch between the natural stance and the athletic stance. The area of the first positioning face 12 is increased, creating a more gradual gradient and can be used to allow the wearer to spread their weight over more toes when in the athletic stance.

In the example illustrated in FIG. 13(o), the points A, B, C, and E are in the same position as in the preferred implementation, with point D moved forward. The adjustment of point D decreases the length of the second positioning face 14 along the edge between points C and D, and can be used to allow the wearer to perform quicker, more explosive movements when in the athletic stance.

In the example illustrated in FIG. 13(p), the points A, B, D, and E are in the same position as in the preferred implementation, with point C moved forward in line with point A. The adjustment of point C makes the second positioning face 14 rectangular, creating an even gradient from the edge between points A and B and the edge between points C and D. Such an even gradient can be used to improve sideways movement.

Figure 13T:
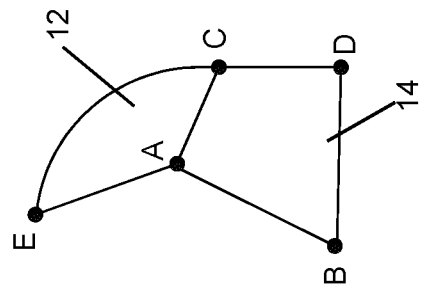
FIGS. 13(a) to 13(t) and 14(a) to 14(p) are bottom views of variations of angled positioning faces.
Figure 13S:
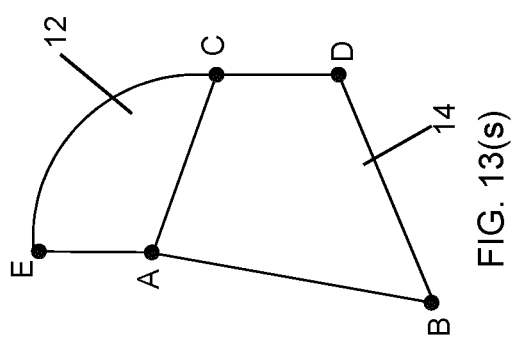
Figure 13R:
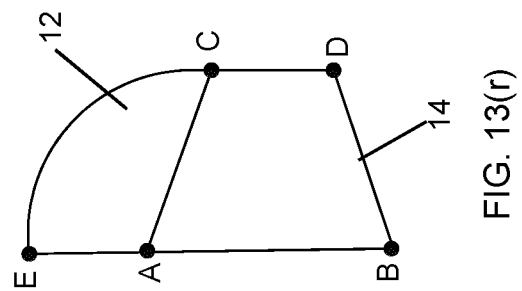
Figure 13Q:
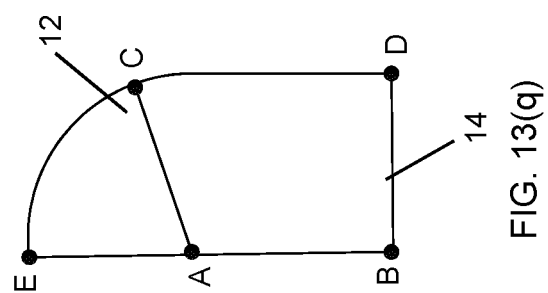

In the example illustrated in FIG. 13(q), the points A, B, D, and E are in the same position as in the preferred implementation, with point C moved forward in front of point A. The adjustment of point C decreases the area of the first positioning face 12, causing the wearer to apply more force through the big toe 22. The second positioning face 14 has an increased area, which can provide greater stability when the wearer engages the ground with the second positioning face 14.

In the example illustrated in FIG. 13(r), the points A, C, D, and E are in the same position as in the preferred implementation, with point B moved backward. The adjustment of point B increases the length of the second positioning face 14 and can allow the wearer to shift their weight slightly backward, behind the ball of the foot 24 when adopting the athletic stance. This example may be used to allow the wearer to more easily move backward.

In the example illustrated in FIG. 13(s), the points A, C, D, and E are in the same position as in the preferred implementation, with point B moved backward and laterally. The adjustment of point B increases the area of the second positioning face 14, specifically increasing the area at the back of the second positioning face 14. This can be used to create a more gradual gradient and improve the transition between the natural stance and the athletic stance.

In the example illustrated in FIG. 13(t), the points C, D, and E are in the same position as in the preferred implementation, with point A moved medially and point B move laterally. The adjustment of point A may be used to allow the wearer to switch between two athletic stances; the wearer may engage the ground with only one of first positioning face 12 or second positioning face 14 by shifting their weight forward or backward. The adjustment of point A also decreases the area of the first positioning face 12, and can be used to cause the wearer to apply more force through the big toe 22 and make faster lateral movements (i.e. propel forward). The adjustment of the point B creates more gradual gradient of the second positioning face 14 and improve the transition between the natural stance and the athletic stance.

Figure 14D:
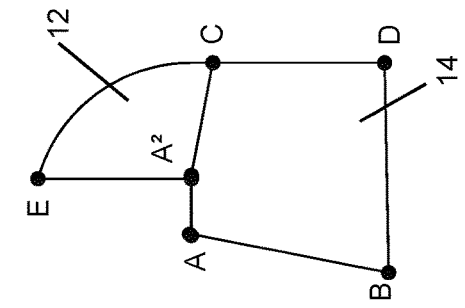
Figure 14C:
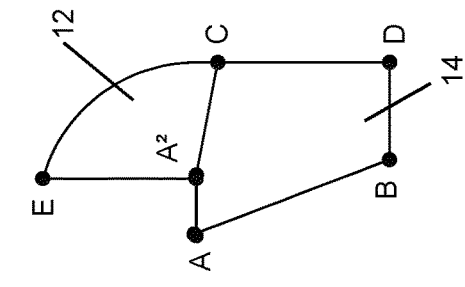
Figure 14B:
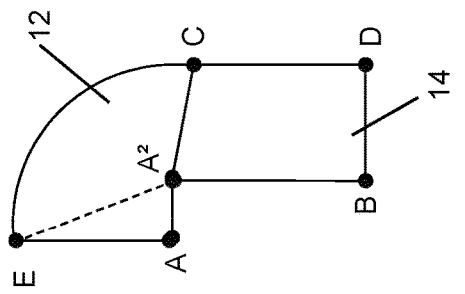

The preferred implementation of the first positioning face 12 and the second positioning face 14 can be further modified by changing the number of vertices or points A through E. Changing the number of vertices can allow the first positioning face 12 and the second positioning face 14 to have different widths, lengths, height and shapes, as shown in FIGS. 14(a) through 14(p).

Figure 14A:
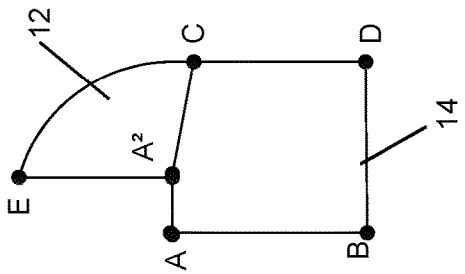
Figure 14H:
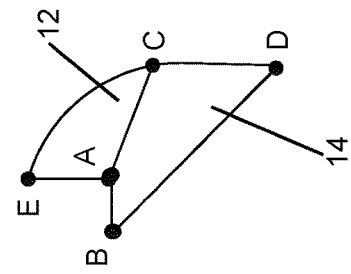
Figure 14G:
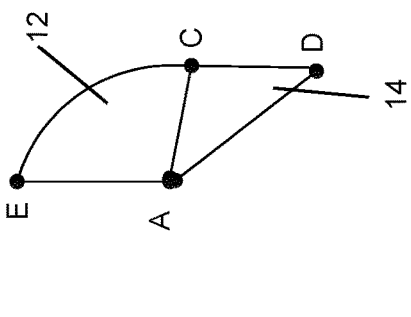
Figure 14F:
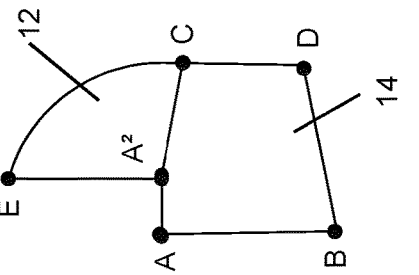

In the example illustrated in FIG. 14(a) an additional point A2 has been included; the first positioning face 12 has vertices at the points A2, C, and E; and the second positioning face 14 has vertices at the points A, B, D, C, and A2. The points C, D, and E are in the same position as in the preferred implementation, and the point A2 is located at the position occupied by point A in the preferred implementation. The points A and B have been moved laterally, resulting in an increased width of the second positioning face 14. The increased width can be used to provide a larger surface for the ball of the foot 24 to balance on and therefore greater stability when the wearer assumes the athletic stance.

In the example illustrated in FIG. 14(b) an additional point A2 has been included; the first positioning face 12 has vertices at the points A, A2, C, and E; and the second positioning face 14 has vertices at the points A2, B, D, and C. The points A, C, D, and E are in the same position as in the preferred implementation. The point B has been moved medially and the point A2 is located medially of point A, resulting in a decreased width of the second positioning face 14. The decreased width of second positioning face 14 decreases the size of second positioning face 14, and can be used to decrease the stability of the wearer in the athletic stance and thus encourage the wearer to only adopt the athletic stance to make fast, explosive movements. Additionally, the size of the primary surface 18 is increased, and can provide the wearer with greater stability when in the natural stance. The curvature of positioning face 12 from point C to point E is centered at point A2, providing the second toe a linear gradient from point A to point E to bear against when the wearer is in the athletic stance.

In the example illustrated in FIG. 14(c) an additional point A2 has been included; the first positioning face 12 has vertices at the points A2, C, and E; and the second positioning face 14 has vertices at the points A, B, C, D, and A2. The points B, C, D, and E are in the same position as in the preferred implementation, and the point A2 is located at the position occupied by point A in the preferred implementation. The point A has been moved laterally to widen the front section of the second positioning face 14, and can cause the wearer to shift their weight slightly forward when engaging the ground with the second positioning face 14 in the athletic stance.

In the example illustrated in FIG. 14(d) an additional point A2 has been included; the first positioning face 12 has vertices at the points A2, C, and E; and the second positioning face 14 has vertices at the points A, B, C, D, and A2. The points C, D, and E are in the same position as in the preferred implementation, and the point A2 is located at the position occupied by point A in the preferred implementation. The point A is moved laterally and the point B is moved laterally further than point A. This example has an increased area of the second positioning face 14, with the back edge between points B and D widened more than the front edge between points A, A2, and C, and can be used to cause the wearer to shift their weight slightly backward. This example may assist the wearer with moving sideways, backwards, or diagonally.

Figure 14E:
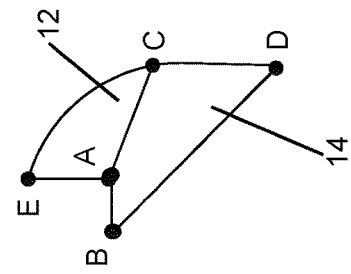

In the example illustrated in FIG. 14(e) an additional point A2 has been included; the first positioning face 12 has vertices at the points A2, C, and E; and the second positioning face 14 has vertices at the points A, B, C, D, and A2. The points C and E are in the same position as in the preferred implementation, and the point A2 is located at the position occupied by point A in the preferred implementation. The points A and B are moved laterally and the point D is moved backwards, increasing the length and width and thus creating a more gradual gradient of the second positioning face 14. This example can be used to provide the wearer with more stability when they engage the ground with the second positioning face 14, and allows the wearer to more easily shift between the natural stance and the athletic stance.

In the example illustrated in FIG. 14(f) an additional point A2 has been included; the first positioning face 12 has vertices at the points A2, C, and E; and the second positioning face 14 has vertices at the points A, B, C, D, and A2. The points C and E are in the same position as in the preferred implementation, and the point A2 is located at the position occupied by point A in the preferred implementation. The points A and B are moved laterally and the point D is moved forward. The adjustment of the points A and B increases the width of the second positioning face 14, and can be used to create a more gradual gradient and providing more stability when the wearer engages the ground with the second positioning face 14 in the athletic stance. The increased width of the second positioning face 14 additionally allows a greater portion of the wearer's foot to bear against the second positioning face 14. The adjustment of the point D causes the wearer to shift their weight forward when they are in the athletic stance.

In the example illustrated in FIG. 14(g) the point B has been removed; the first positioning face 12 has vertices at points A, C, and E; and the second positioning face 14 has vertices at the points A, C, and D. The points A, C, D, and E are in the same position as in the preferred implementation. The removal of point B can be used to allow the wearer to perform quicker motions when in the athletic stance, and increases the area of the primary surface 18 to provide greater stability when the wearer is in the natural stance.

In the example illustrated in FIG. 14(h) the points A, C, D, and E are in the same positions as in the preferred implementation, with the point B moved laterally and forward to a position forward of the point C, and lateral to point A. The width of the front of the second positioning face 14 is increased, while the width of the back of the second positioning face 14 is decreased, and can be used to cause the wearer to shift their weight further forward when in the athletic stance.

Figure 14I:
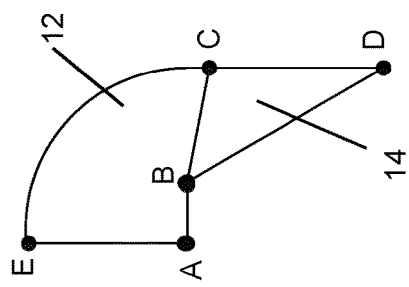

In the example illustrated in FIG. 14(i) the points A, C, D, and E are in the same positions as in the preferred implementation, with the point B moved forward of the point C and medial to the point A. The width and area of the second positioning face 14 is decreased, allowing the wearer to adopt the athletic stance only when making quick lateral movements. This example may be used to shift the wearer's weight further forward when adopting the athletic stance.

Figure 14J:
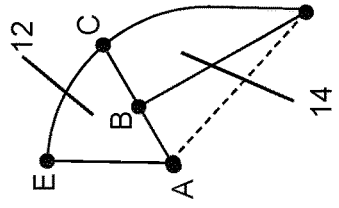

In the example illustrated in FIG. 14(j) the points A, D, and E are in the same position as in the preferred implementation. The point C is moved forward of the point A, and the point B is moved forward and medial to the point A. The adjustment of the point C decreases the area of the first positioning face 12, and can be used to cause the wearer to transfer more force through their toes when engaging the ground with the first positioning face 12. In this example, the point B may be located anywhere on the edge between the points A and C. If the point B is located close to the point A, including being coincident with the point A, the second positioning face 14 is triangular in shape with a larger area under the front of the ball of the wearer's foot 24. Such a second positioning face 14 may cause the wearer to shift their weight forward when adopting the athletic stance, and can be used to assist the wearer with moving diagonally. If the point B is moved towards point C, for example if the point B is located halfway between the points A and C, the width and area of the second positioning face 14 is decreased, and can be used to allow the wearer to adopt the athletic stance only when making quick lateral movements.

Figure 14K:
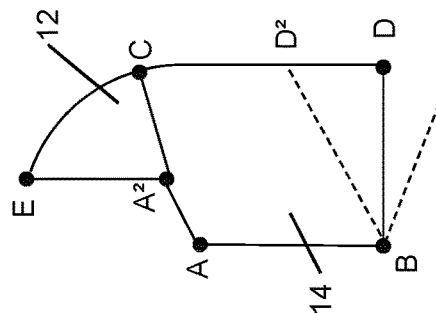

In the example illustrated in FIG. 14(k) an additional point A2 has been included; the first positioning face 12 has vertices at the points A2, C, and E; and the second positioning face 14 has vertices at the points A, B, C, D, and A2. The point E is in the same position as in the preferred implementation, and the point A2 is located at the position occupied by point A in the preferred implementation. The point C is moved forward along the contour of the sole 10, decreasing the area of the first positioning face 12, and can be used to cause the wearer to transfer more force through their toes when engaging the ground with the first positioning face 12. The point A is moved backward and laterally, the point B is moved laterally, and the point D is optionally moved forward to $D^2$ or backward to $D^1$. The adjustment of the points A and B increase the width of the second positioning face 14, and can be used to provide greater stability when the wearer adopts the athletic stance. The point D may remain in the same position as in the preferred implementation, be moved backward (to $D^1$) to further increase the area of the second positioning face 14 and provide even greater stability when the wearer adopts the athletic stance, or is moved forward (to $D^2$) causing the wearer to shift their weight further forward when adopting the athletic stance.

Figure 14L:
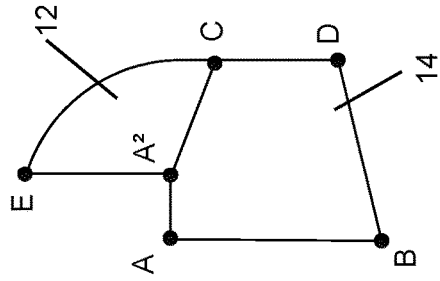

In the example illustrated in FIG. 14(l) an additional point A2 has been included; the first positioning face 12 has vertices at the points A2, C, and E; and the second positioning face 14 has vertices at the points A, B, C, D, and A2. The points C, D, and E are in the same positions as in the preferred implementation, and the point A2 is located at the position occupied by point A in the preferred implementation. The point A is moved laterally, and the point B is moved backward and laterally. The adjustment of the points A and B increases the area of the second positioning face 14, and can be used to provide greater stability when the wearer adopts the athletic stance.

Figure 14M:
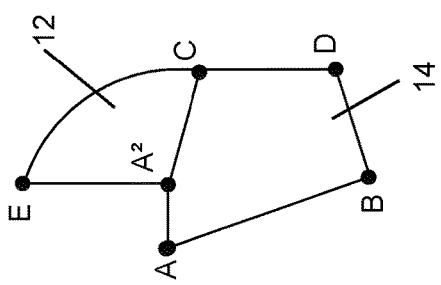

In the example illustrated in FIG. 14(m) an additional point A2 has been included; the first positioning face 12 has vertices at the points A2, C, and E; and the second positioning face 14 has vertices at the points A, B, C, D, and A2. The points C, D, and E are in the same positions as in the preferred implementation, and the point A2 is located at the position occupied by point A in the preferred implementation. The point A is moved laterally, and the point B is moved backward. The adjustment of the point A increases the width of the second positioning face 14 at the front of the ball of the wearer's foot 24, and can cause the wearer to shift their weight further forward when adopting the athletic stance. The adjustment of the point B creates a more gradual gradient, and can be used to improve the transition between the natural stance and the athletic stance.

Figure 14N:
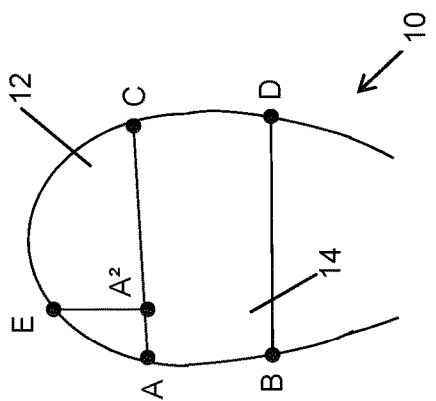

In the example illustrated in FIG. 14(n) an additional point A2 has been included; the first positioning face has vertices at the points A2, C, and E; and the second positioning face 14 has vertices at the points A, B, C, D, and A2. It may be noted that point D remains in the same position, and point C has moved upwards in position. The points E and A2 can be moved laterally. In this way, the position of point C provides more surface area for the second positioning face to use. The width of the first positioning face 12 is increased, and can allow the wearer to transfer force through a greater number of toes when engaging the ground with the first positioning face 12. The second positioning face 14 spans the entire width of the sole 10, wherein the points A and B are located on the lateral edge of the sole 10 and the points C and D are located on the medial edge of the sole 10. The increased width of the second positioning face 14 allows the wearer to use the entire forefoot when adopting the athletic stance. This example can be used to provide greater traction to the wearer when accelerating or decelerating laterally, or to provide greater control when jumping.

Figure 14O:
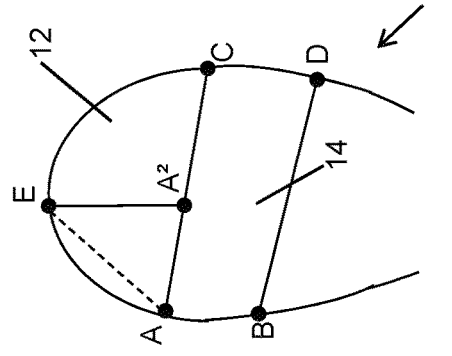
Figure 14P:
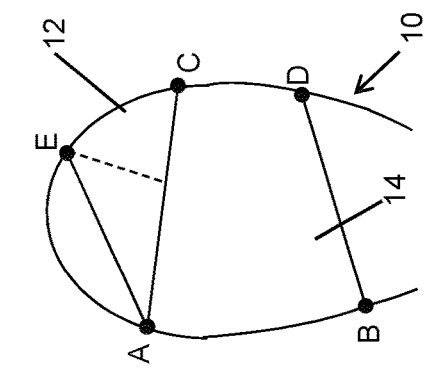

In the example illustrated in FIG. 14(o) an additional point A2 has been included; the first positioning face has vertices at the points A2, C, and E; and the second positioning face 14 has vertices at the points A, B, C, D, and A2. The points C and E are in the same positions as in the preferred implementation, and the point A2 is located at the position occupied by point A in the preferred implementation. It may be noted that point D is moved down to provide more surface for the ball of the foot 24 to utilize, in order to better stabilize the wearer's balance, and to create a more gradual gradient. This can also improve the transition between the natural stance and the athletic stance. The second positioning face 14 spans the entire width of the sole 10, wherein the points A and B are located on the lateral edge of the sole 10 and the points C and D are located on the medial edge of the sole 10. The increased width of the second positioning face 14 allows the wearer to use the entire forefoot when adopting the athletic stance. This example can be used to provide greater traction to the wearer when accelerating or decelerating laterally, or to provide greater control when jumping.

In the example illustrated in FIG. 14(p) the first positioning face has vertices at the points A, C, and E; and the second positioning face 14 has vertices at the points A, B, C, and D. The second positioning face 14 spans the entire width of the sole 10, wherein the points A and B are located on the lateral edge of the sole 10 and the points C and D are located on the medial edge of the sole 10. The point E is moved medial along the contour of the sole 10. The adjustment of the point E decreases the length of the first positioning face 12, and can allow the wearer to pivot quicker. The increased width of the second positioning face 14 allows the wearer to use the entire forefoot when adopting the athletic stance, for example to provide greater traction to the wearer when accelerating or decelerating laterally, or to provide greater control when jumping. The point B is also moved backward to create a more gradual gradient, and can be used to improve the transition between the natural stance and the athletic stance.

It should be understood that FIGS. 12 through 14 are meant only as illustrative examples, and that the positioning faces 12, 14, 16 may be of any geometry.

The example implementations of the positioning faces 12, 14 shown in FIGS. 12(a) through 12 (j) illustrate different heights of the points A, B, C, D, E. The example implementations of the positioning faces 12, 14 shown in FIGS. 13 and 14 illustrate different lateral positions of the points A, B, C, D, E. It should be appreciated that the example implementations described herein may be combined in any way. That is, the heights of the points A, B, C, D, and E as described by one of FIGS. 12(a) through 12(j) can be can be combined with the lateral positions as described by one of FIGS. 13 and 14. For example, the positioning faces 12, 14 may be implemented with the heights of the points A, B, C, D, E as illustrated by FIG. 12(c) and the lateral position of the points A, B, C, D, E as illustrated by FIG. 13(e).

A method of creating a customized shoe sole to fix the defects in a user's natural gait is provided herein. In one embodiment, a gait analysis is conducted and the gait of a user is measured using gait analysis techniques. Based on the results of the gait analysis, a customized sole with positioning faces can be created for each user. The positioning faces will compensate for and fix problems in the natural gait of the user. The customized sole can be created using features as required by the results of the gait analysis. For instance, the gait analysis will determine the degree of pronation or supination of a user. If the user is determined to have over-supinated ankles, a sole with positioning faces on the medial side can be created to eliminate the over-supinated ankles. The features used to create the customized sole are described herein as alternative embodiments of the sole. The features can be used alone, or in combination to create a fully customized sole with positioning faces.

Figure 15:
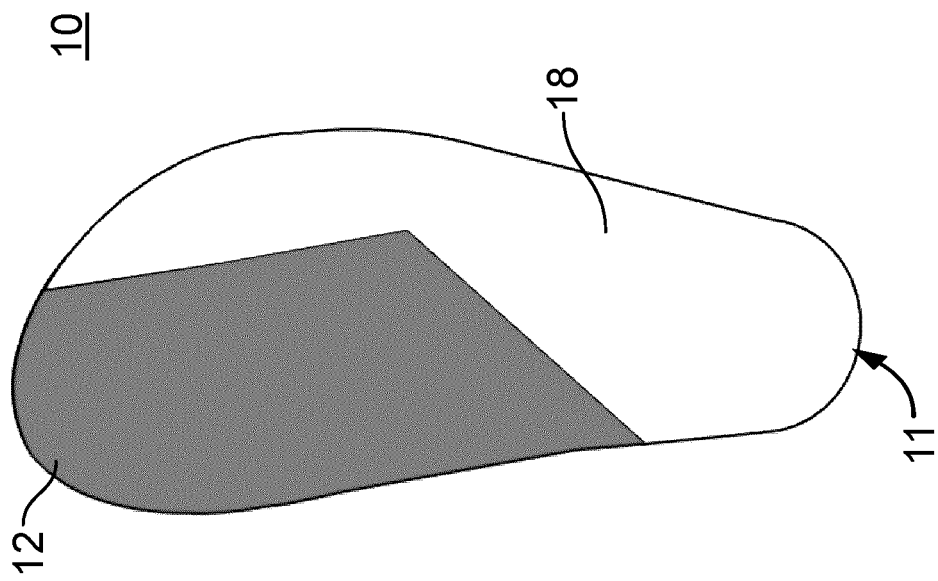
FIG. 15 is a bottom view of an example of a sole with one positioning face angled in one direction.

FIGS. 15-26 show alternative embodiments of the sole 10. In one embodiment, the sole only comprises one positioning face 12, and the first positioning face 12 is angled in the direction of the arrow, as seen in FIG. 15. The positioning face 12 is illustrated as planar; however, it should be appreciated that the positioning face 12 may be convex, concave, or otherwise non-planar.

Figure 16B:
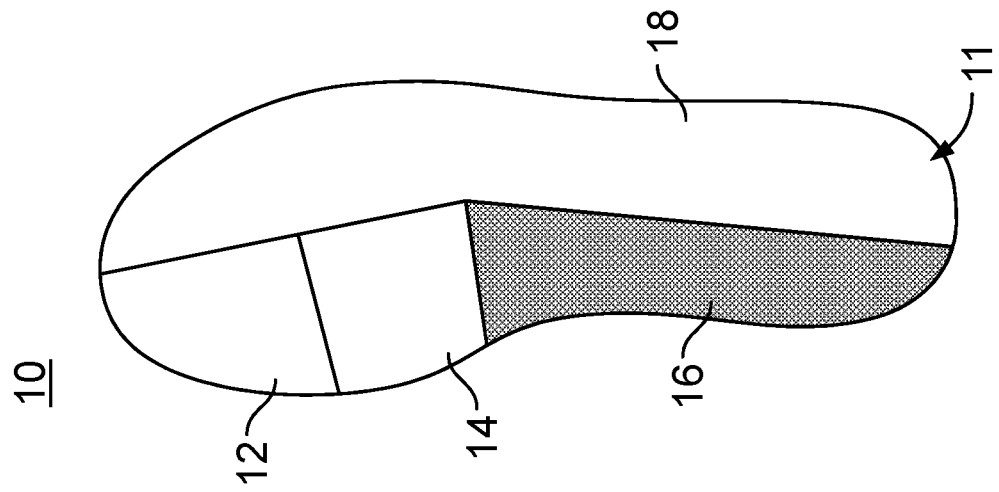
FIGS. 16a and 16b show the bottom view of an example of a sole with three positioning faces.
Figure 16A:
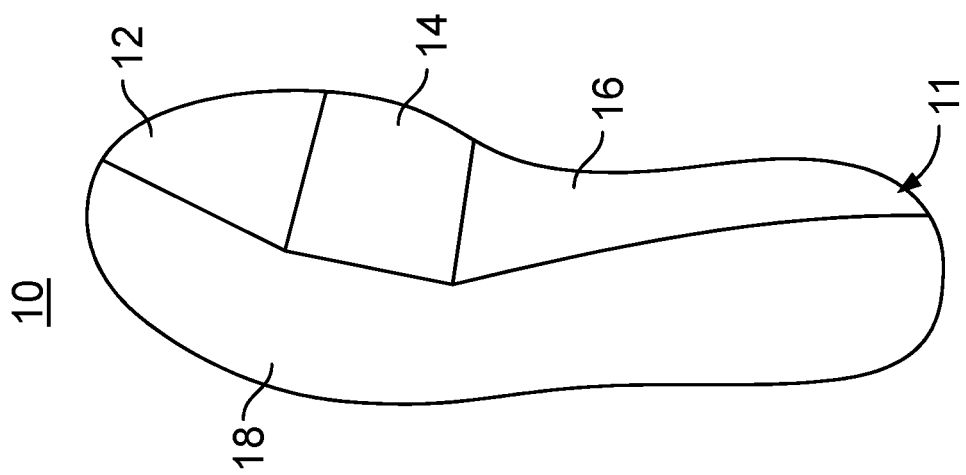

In another embodiment, the sole 10 comprises a third positioning face 16 located on the heel of the sole, as seen in FIG. 16. A positioning face located towards the back of the foot can help provide greater stability to the user and can be accessed when the user shifts their weight backward. It is particularly useful in sports where foot placement is critical such as golf, baseball, curling, etc.

In yet another embodiment, one positioning face can be lower to, or higher from the ground than another positioning face. This embodiment can be seen in FIGS. 17a and 17b. In FIG. 17a, the first positioning face 12 is closer to the ground than the second positioning face 14; allowing the wearer to use their toes and the front of their foot to generate more force. Having a first positioning face lower than a second positioning face is useful during running and jumping. In FIG. 17b, the second positioning face 14 is closer to the ground than the first positioning face 12; allowing the user to the ball of their foot 24 to assist in lateral movement. This embodiment allows the user to lean towards a specific direction to create more torque with less effort and thus it can be useful in sports such as tennis and basketball.

The positioning face may also include cushioning 40 to help transition from the primary surface of the sole to one or more of the positioning faces. In one embodiment, the first positioning face 12 is cushioned to assist the user in moving forward. Alternatively, the second positioning face 14 can also be cushioned to assist the user in moving backward. The cushion 40 may be soft or firm, or a combination thereof, depending on the application required by the user. The cushioning 40 may also absorb impact, for example, when the user jumps and needs to land the fall in a safe manner. FIG. 18a shows the cushion 40 at the first positioning face 12. FIG. 18b shows the cushion 40 at the second positioning face 14. Alternatively, the cushion 40 can be placed at both positioning faces 12, 14, as shown in FIGS. 18*c* and 18*d*. One positioning face may be cushioned with a compressible material and another positioning face cushioned with a firm material or, may not be cushioned at all. The cushion can be applied to the entire positioning face. The cushion can also be applied to the third positioning face 16 (not pictured).

The outsole may comprise a tread 42 or flexible grooves 44. In one embodiment, the tread 42 is attached on the underside of the midsole and positioning face. The tread may be flush with the ground or, it can be shaped to contour the positioning face, as shown in FIGS. 19*a* and 19*b* respectively. Flexible grooves 44 can be installed on the outsole for additional support, as shown in FIG. 20*a*. When the user weighs down on the first positioning face 12, the grooves 44 flex and spread apart, as shown in FIG. 20*b*.

Figure 21A:
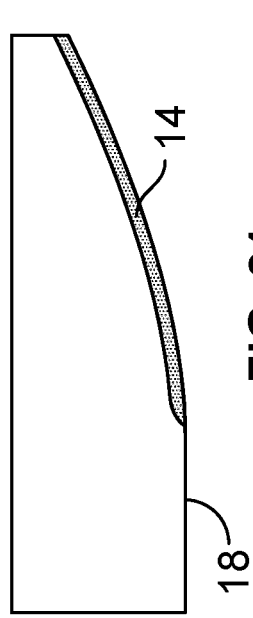
FIG. 21a is a cross sectional view of an embodiment of the sole with a curved transition between the positioning faces and primary surface.
Figure 21B:
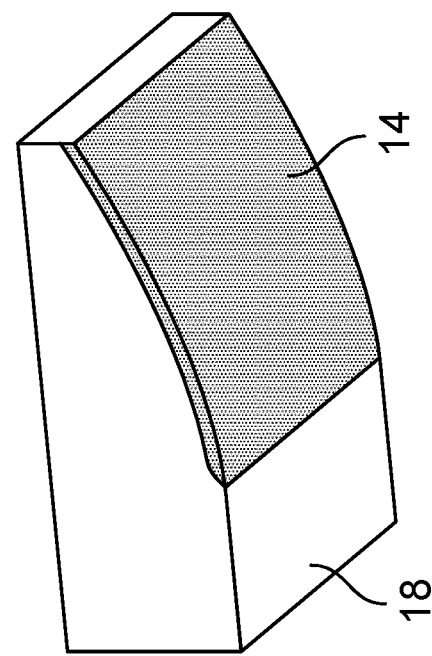

The sole and the positioning faces 12, 14, 16 can be curved or rounded to make the transition between the lateral and medial or the first, second and third positioning faces 12, 14, 16 more natural. This embodiment can be observed in FIGS. 21*a* and 21*b*. FIG. 21*a* shows a partial cross sectional view of an embodiment of the sole wherein the transition between the primary surface 18 and the second positioning face 14 is curved. FIG. 21*b* shows a bottom perspective view of the same.

In another embodiment of the sole design, positioning face attachment members 46 can be detachably attached to a positioning face. The sole can have no positioning faces when the attachment member 46 is attached to having at least one or more positioning faces when the attachment member is detached. FIG. 22*a* shows a cross sectional view of the sole with positioning face attachment members. FIG. 22*b* shows the attachment member 46 in isolation. The attachment member can be detachably attached using a Velcro mechanism, mechanical fasteners, zippers, magnets, or a combination of these mechanisms. The plate 50 may also be embedded into the outsole of the shoe such that it is attached in a more permanent way.

Transition mechanisms can be added to the sole to assist in implementing the positioning faces of the sole. FIG. 23 show cross-sectional views of the sole with various transitioning mechanisms. The outsole comprises a plate 50 and a hinge 48 such that the plate 50 is biased to the natural stance and can move to the athletic stances when the user shifts their weight forward. The sole can optionally comprise a hollow space 52, an air cavity, or a compressible material 54 such that the sole 50 can smoothly transition between the stances. The compressible material may be constructed of a foam, rubber, plastic, fluids, gases, and the like. The material may be 3D printed, injection molded, overmolded, sprayed or filled into the space.

Figure 23A:
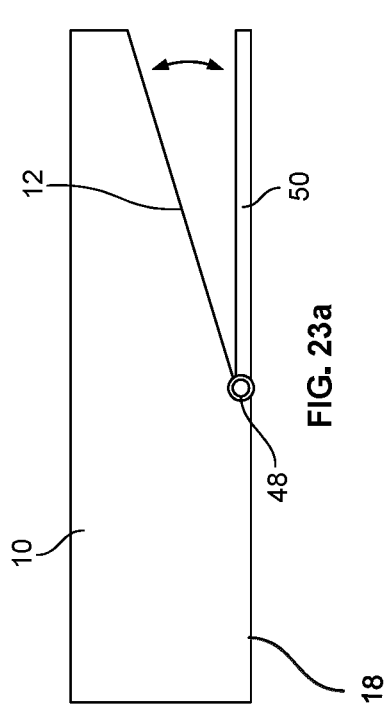
FIG. 23a shows a partial cross-sectional view of the sole with a hinge mechanism.
Figure 23B:
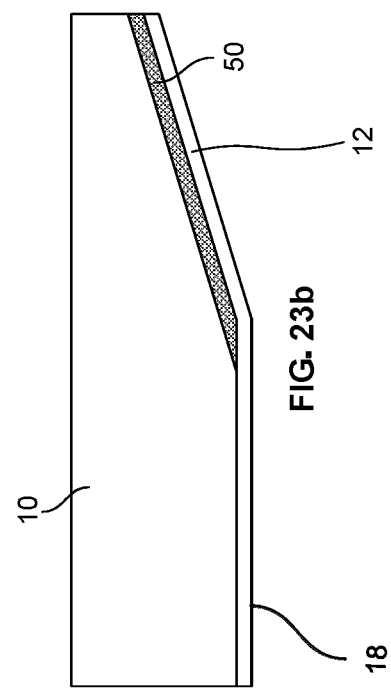
FIG. 23b shows a partial cross-sectional view of the sole with a fixed plate embedded or used with the positioning face.

FIG. 23*a* shows that the plate 50 can be open and shut to shift between the natural stance and the athletic stance. FIG. 23*b* shows a fixed plate 50 embedded within the positioning faces. The plate 50 can be detachably fixed to the positioning face via magnets in combination with the hinge mechanism to maintain the athletic stance. The plate 50 can take shape of the positioning faces being used. While the plate 50 is engaged with the ground, the heel 23 or primary surface 18 may not necessarily be lifted from the ground.

FIG. 23*c* shows that the space between the outsole 66 and the positioning face 12 can be filled with air 52. FIG. 23*d* shows the space between the outsole 66 and positioning face 12 can be filled with a compressible material 54 such as foam. The outsole 66 can be detachably fixed to the positioning face via magnets in combination with the hinge mechanism to maintain the athletic stance. The outsole 66 can take shape of the positioning faces being used. The heel portion 23 and/or primary surface 18 may be flushed with the positioning faces 12, 14 if the wearer does not apply pressure on top of the positioning faces, to engage the positioning faces in the athletic stance. While the outsole 66 is engaged with the ground, the heel 23 or primary surface 18 may not necessarily be lifted from the ground.

In an alternative embodiment, a lever mechanism 58 can be added to the sole to assist the user transition from the lateral side to the medial side of the sole. FIG. 24 provides a cross-sectional view of a sole with a lever mechanism. The sole can optionally comprise a hollow space or an air cavity 56 for a smooth transition between the positioning faces. FIG. 24*a* shows the lever 58 in its biased position, whereas FIG. 24*b* shows the lever in an active state. In another embodiment, a wedge 60 can be placed in between the first and second faces 12, 14 to separate the force being used from the first and the second positioning faces. While using the first positioning face, the wedge can help exert more force from the user's toes, as seen in FIG. 25. It is understood that the mechanism may comprise multiple geometries, sizes, materials, or a combination thereof.

Figure 26A:
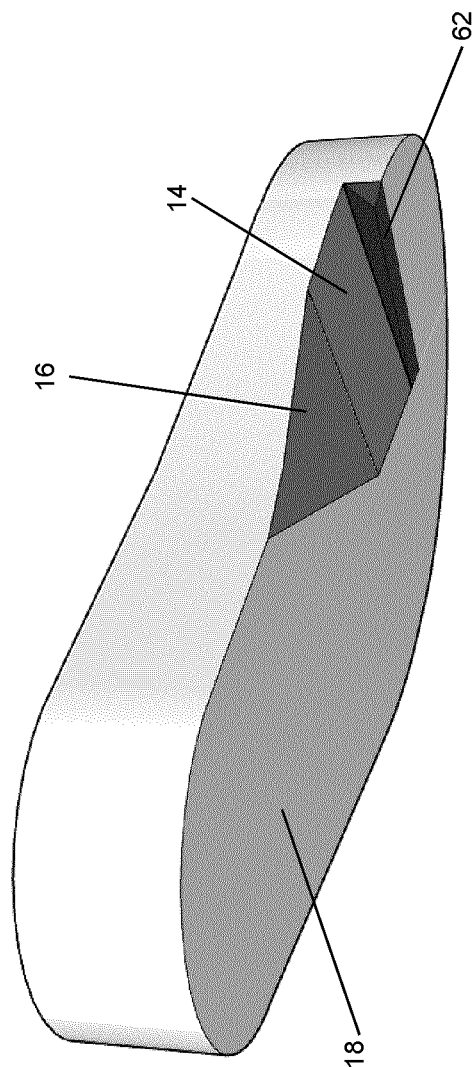
FIGS. 26a and 26b show partial cross-sectional views of the sole with a flap mechanism.
Figure 26B:
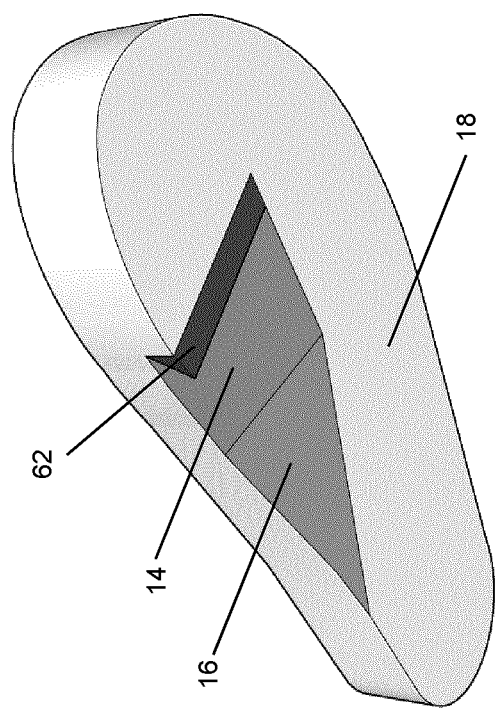

In yet another embodiment, a flap mechanism 62 can be added to the sole, as seen in FIGS. 26*a* and 26*b*. The flap 62 can be compressed and spread out under a positioning face to provide greater surface area for the big toe 22 to lift off with. Having a greater surface area will provide greater traction for the foot, giving greater stability to the user, while still having the ability to use the second positioning face to change directions laterally. This feature can be used in any of the 3 positioning faces (not shown in the figures).

FIG. 27 shows a sample gait chart of a left foot while taking one step. Either the heel of the foot 23 or the ball of the foot 24 is activated at any given point. During heel strike, the user may activate the third positioning face near the heel and push forward into the natural stance. Once the heel is lifted, the user may transition into the athletic stance for toe off position. The shoe sole with positioning faces has been created to fix a user's actual gait and convert it into an ideal gait. The gait analysis of the user will help determine which features of the sole with positioning faces will be used to create a customized shoe sole. The features can be used in combination with each other or alone to help create an ideal gait for each user. The customized sole can be used to compensate for any irregularities in the user's natural gait. Most of the pressure when walking is put on the heel of the foot 23, ball of foot 24 and the big toe 22, and having a sole with positioning faces can help relieve the pressure.

FIG. 27A illustrates degree of pronation or supination (ankle tilt) when walking. The walking cycle begins at heel strike and continues to midstance and finishes at toe off. FIG. 27B shows the back view of a right leg, ankle and foot in motion with reference to FIG. 27A. FIG. 27C shows the medial view of a right leg with reference to FIGS. 27A and B. FIG. 27D shows the bottom view of a right foot, regions of higher pressure are shaded black with reference to FIG. 27A-C.

Figure 28:
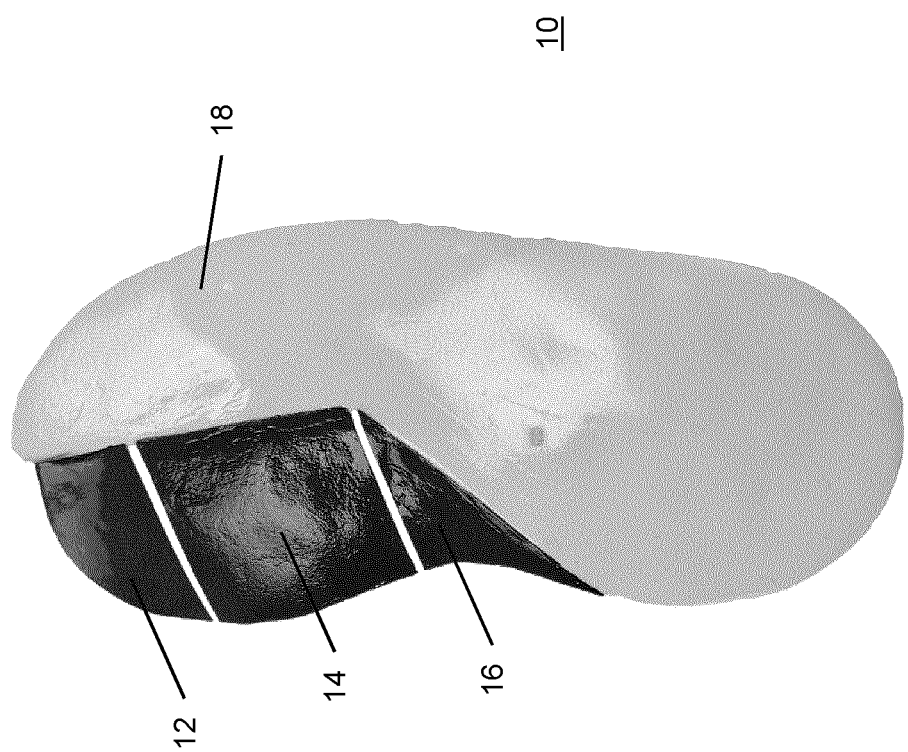
FIG. 28 is a bottom view of an example of a left sole with three positioning faces.
Figure 29:
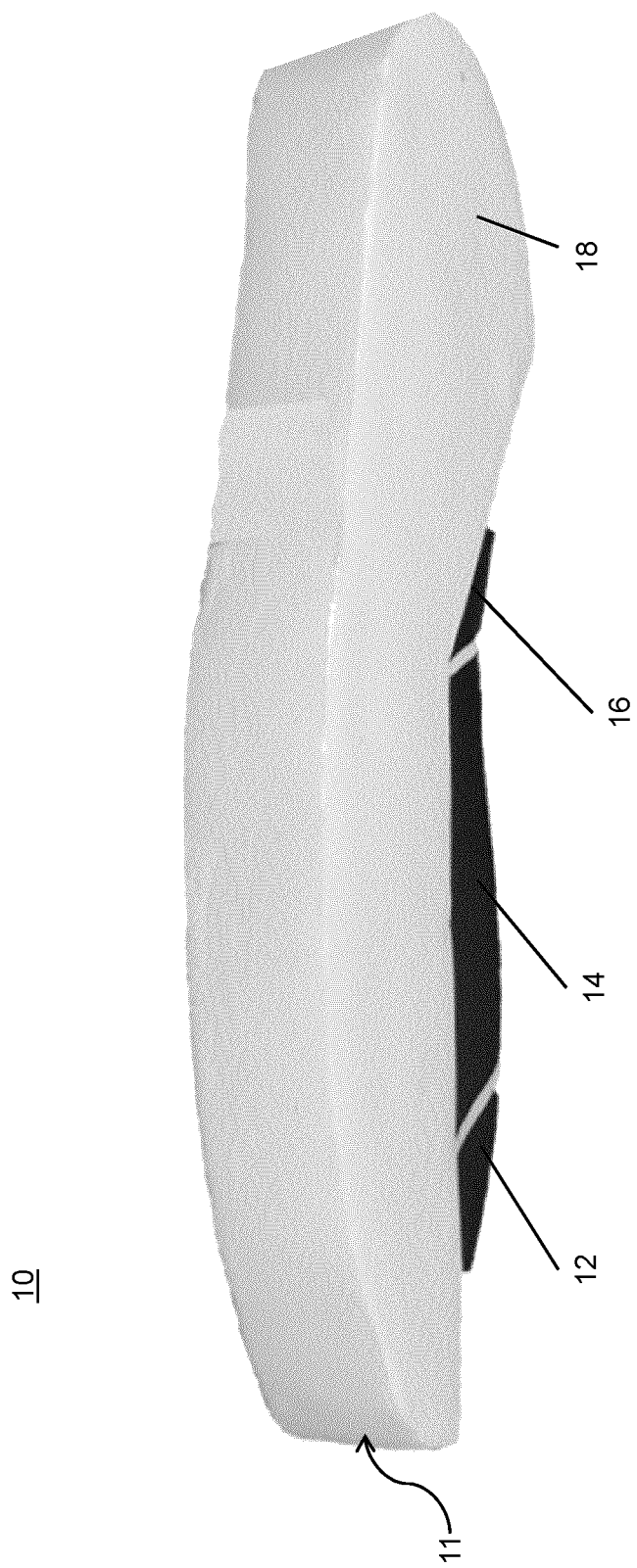
FIG. 29 is a lateral view of the sole in FIG. 28.

FIGS. 28-36 illustrate prototypes of the sole having multiple positioning faces. FIG. 28 shows the bottom view of the left sole having three positioning faces. The first positioning face 12 is angled downward, away from the primary surface 18. This embodiment also has a second angled positioning face 14 and a third angled positioning face 16. FIG. 29 shows a lateral view of the sole from FIG. 28. The angles of the three positioning faces can vary.

Figure 30:
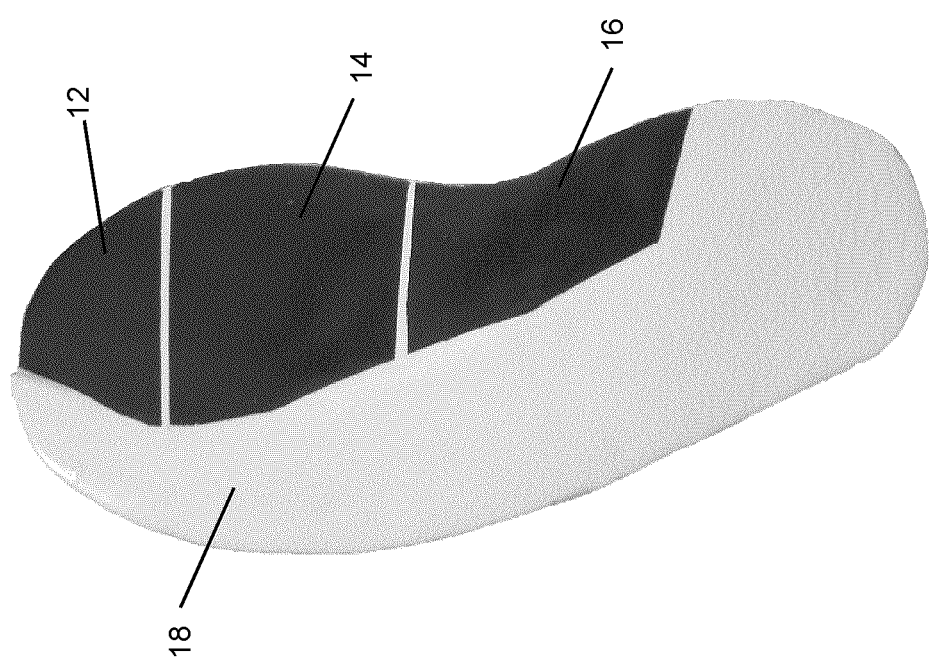
FIG. 30 is a bottom view of an example of a right sole with three positioning faces.
Figure 31:
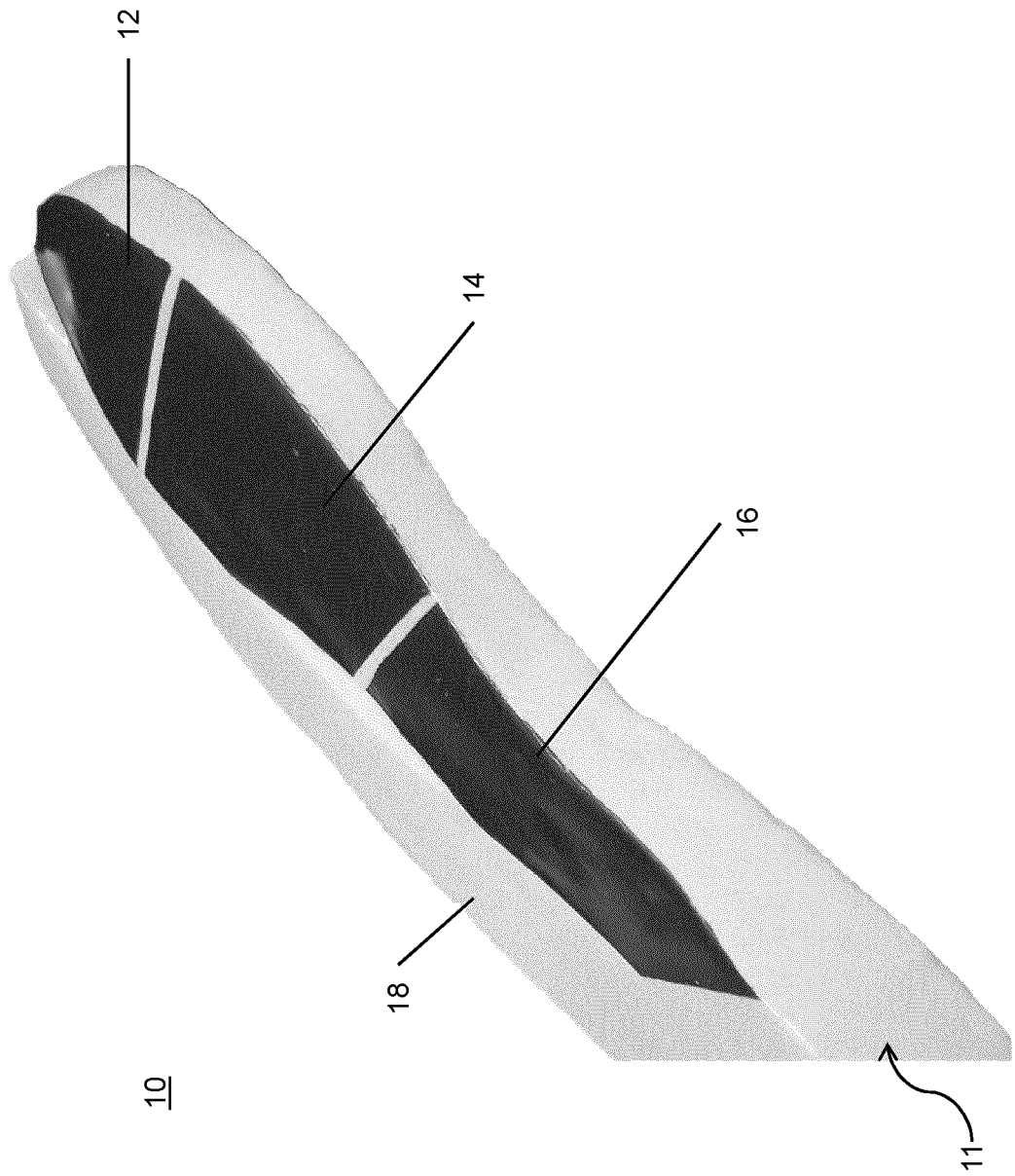
FIG. 31 is a bottom perspective view of the sole in FIG. 30.
Figure 32:
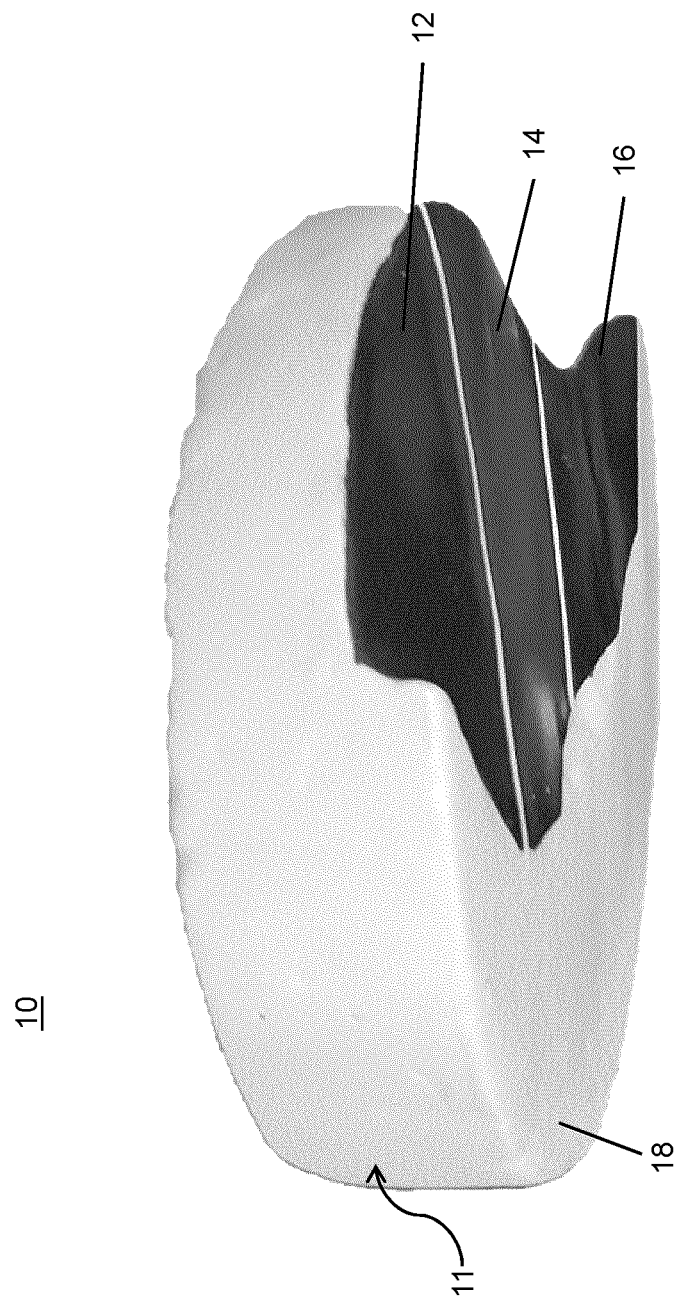
FIG. 32 is a front view of the sole in FIG. 30.

FIG. 30 shows another embodiment of a sole with three positioning faces. In this embodiment, the positioning faces have smaller angles. FIG. 31 shows a bottom perspective view of the sole shown in FIG. 30. The first positioning face 12 is angled forward, while the second 14 and third positioning 16 faces are angled inward. FIG. 32 shows a front view of the sole in FIG. 30.

Figure 33:
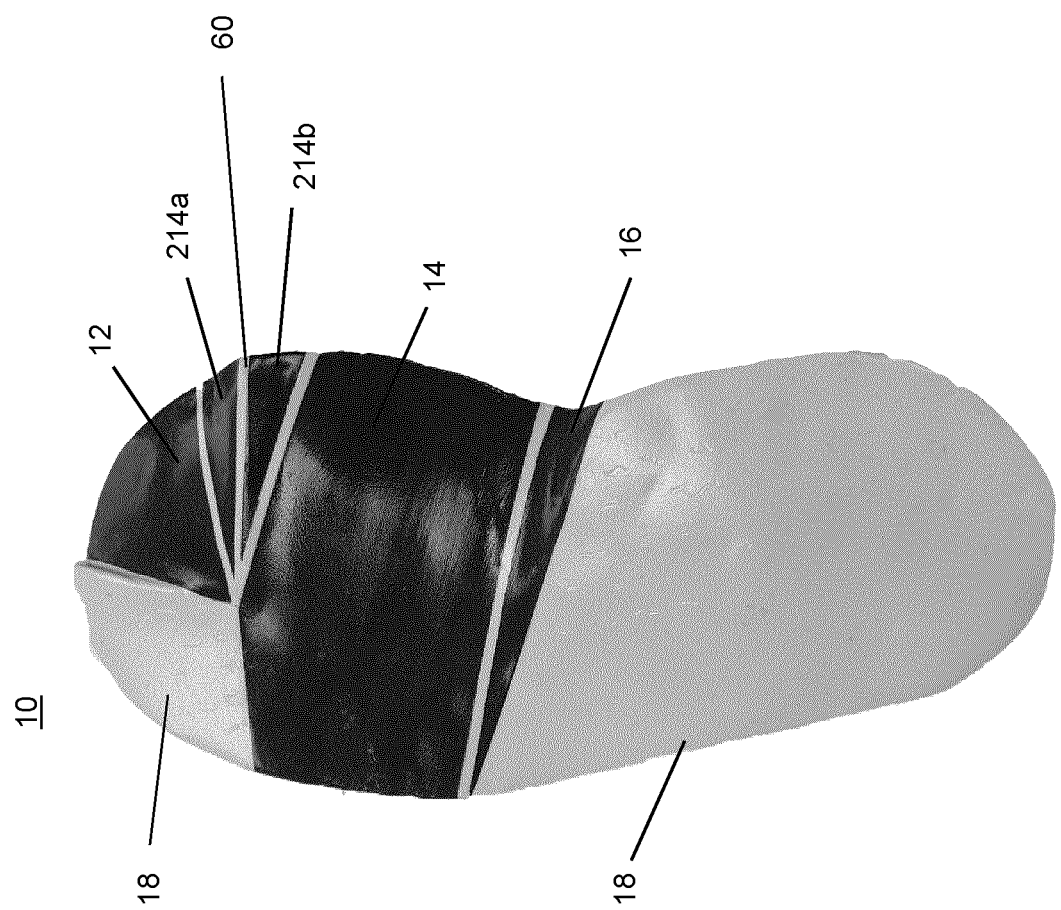
FIG. 33 is a bottom view of an example of a right sole with five positioning faces.

FIG. 33 shows a bottom view of an example of a right sole with five positioning faces. In this instance, there are 2 positioning faces between the first positioning face 12 and second positioning face 14, which are angled to create a wedge in the sole. A wedge 60 can be placed in between the first and second faces 12, 14 to allow the user to exert force from their toes, as seen in FIGS. 25 and 33. It is understood that the mechanism may comprise multiple geometries, sizes, materials, or a combination thereof.

Figure 34:
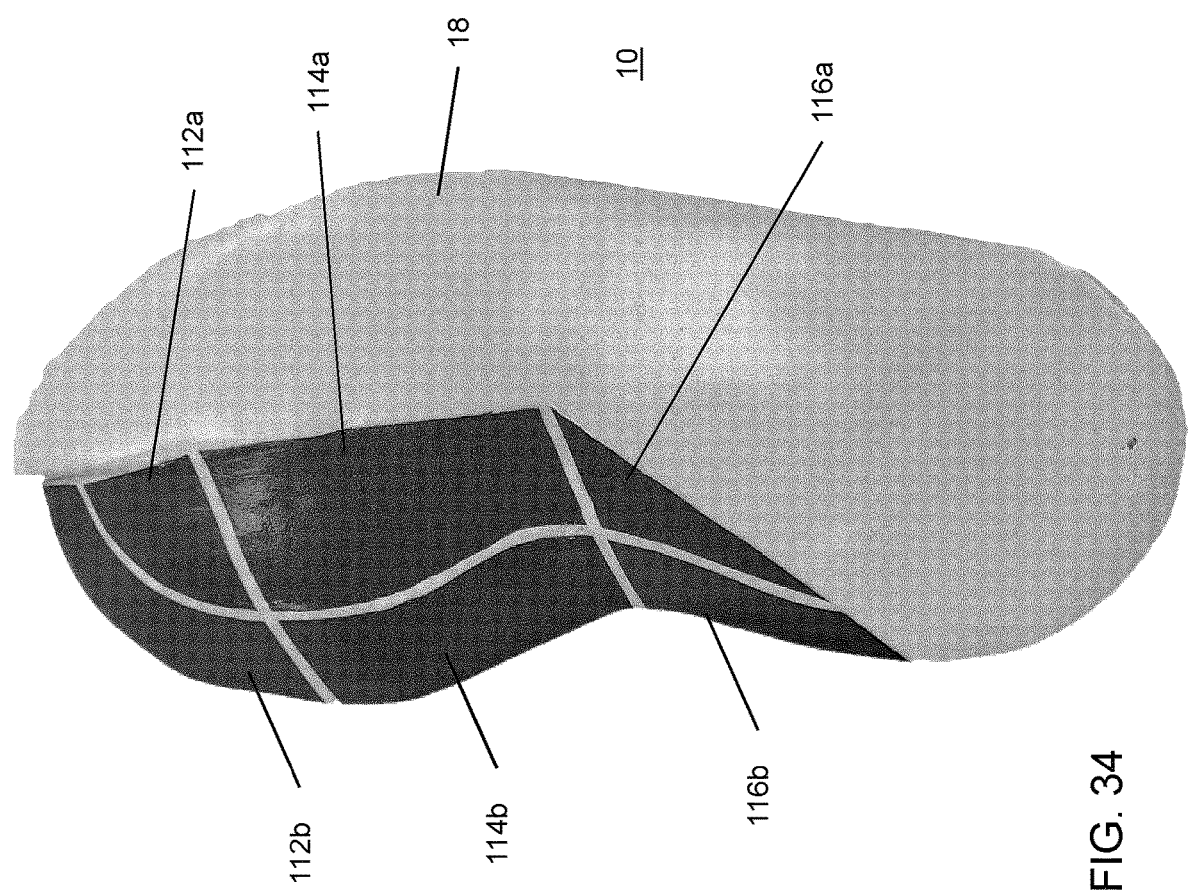
FIG. 34 is a bottom view of an example of a left sole with curved positioning faces and subfaces.
Figure 35:
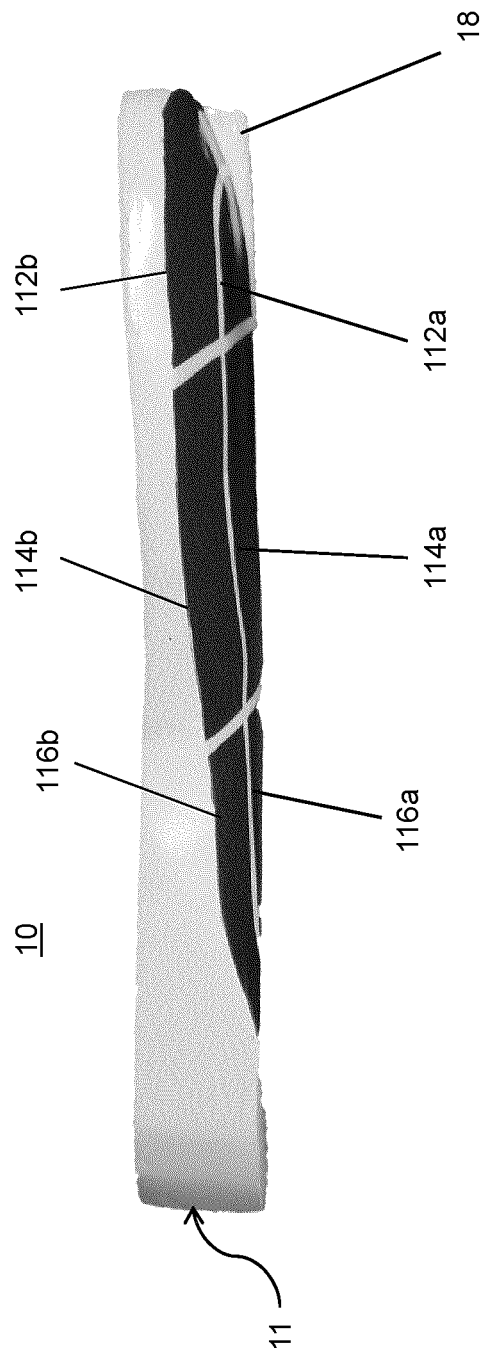
FIG. 35 is a medial view of the sole in FIG. 34.
Figure 36:
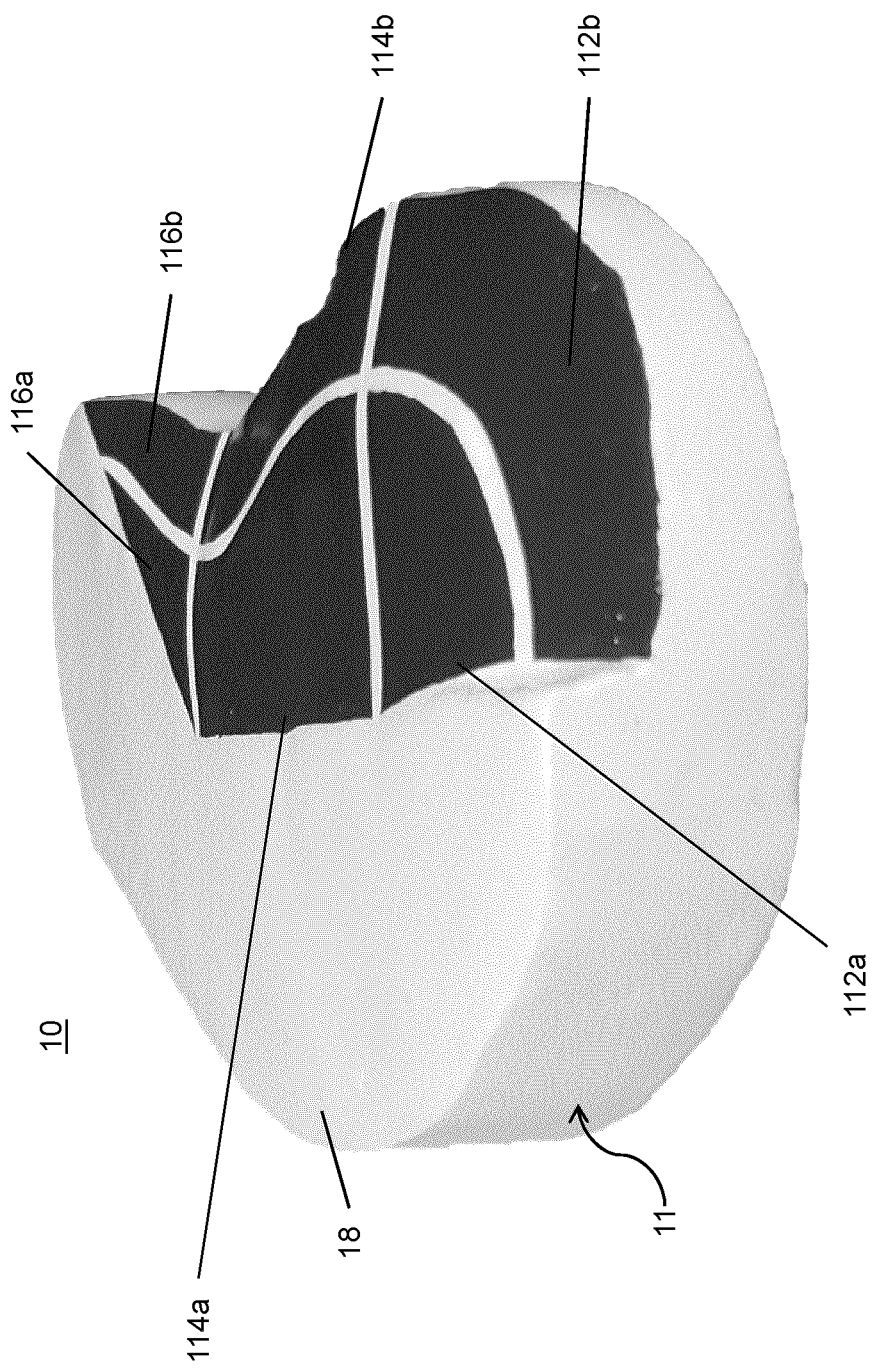
FIG. 36 is a front upside-down view of the sole in FIG. 34.

FIG. 34 shows a bottom view of an example of a left sole with curved positioning faces and subfaces. In this embodiment, the first positioning face 12, the second positioning face 14 and the third positioning face 16 are curved outward. The first positioning face has been subdivided into two subfaces, 112a and 112b. The second positioning face has been subdivided into two subfaces, 114a and 114b. The third positioning face has been subdivided into two subfaces, 116a and 116b. FIG. 35 is a medial view of the sole in FIG. 34. FIG. 36 is a front upside-down view of the sole in FIG. 34.

Figure 37:
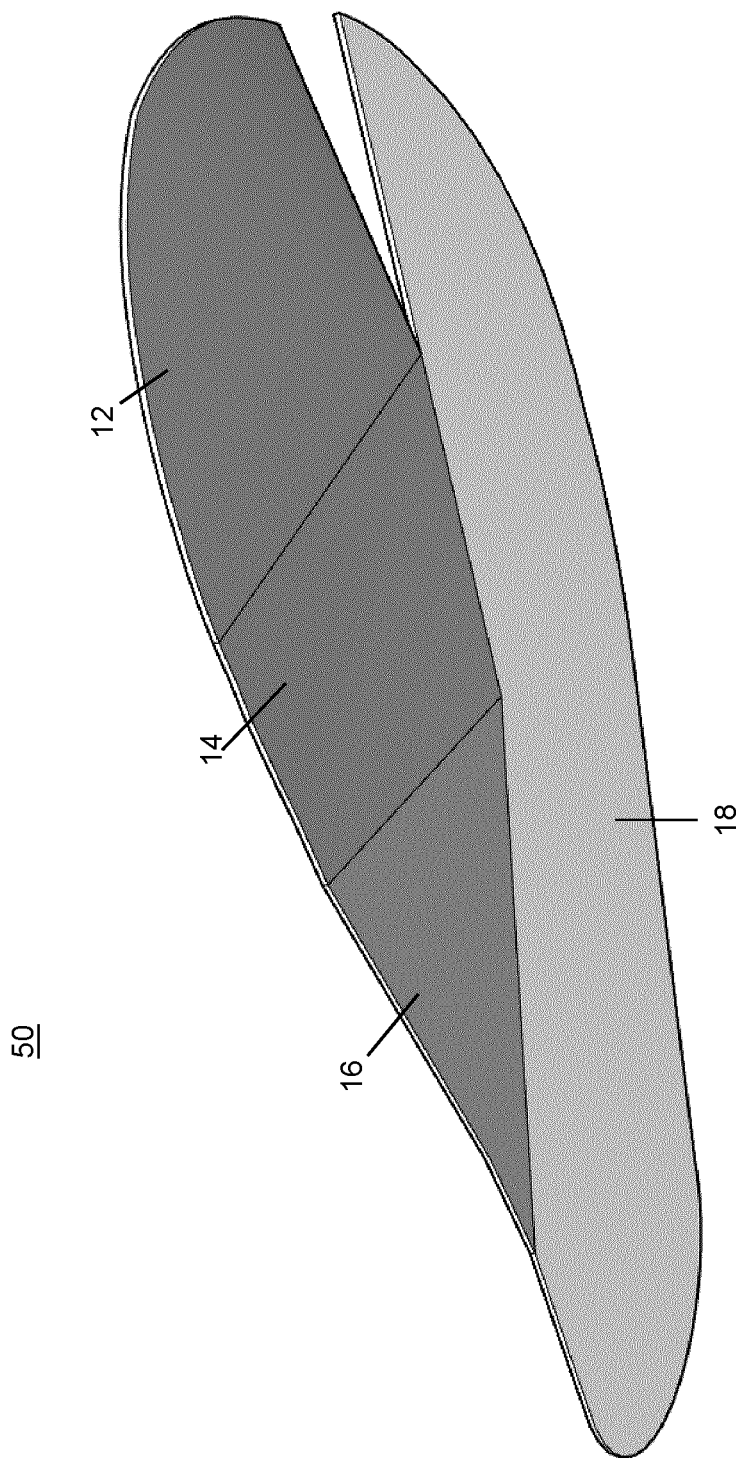
FIG. 37 is a bottom perspective view of a plate with three positioning faces.

FIG. 37 shows a bottom perspective view of a plate 50 having a first positioning face 12, a second positioning face 14, and a third positioning face 16. Alternatively, the plate can have any number or combination of positioning faces. The plate 50 can be detachably fixed to the bottom of a shoe sole to transform an ordinary shoe into a shoe with positioning faces. FIG. 38 shows a top perspective view of the plate 50 shown in FIG. 37. The top of the plate 50 contains magnets 64 to detachably fixed to the bottom of a shoe sole also containing magnets. Alternatively, the plate 50 can be detachably fixed to the sole of a shoe using adhesives, Velcro strips, mechanical fasteners, screws, or any combination thereof.

For simplicity and clarity of illustration, where considered appropriate, reference numerals may be repeated among the figures to indicate corresponding or analogous elements. In addition, numerous specific details are set forth in order to provide a thorough understanding of the examples described herein. However, it will be understood by those of ordinary skill in the art that the examples described herein may be practiced without these specific details. In other instances, well-known methods, procedures, and components have not been described in detail so as not to obscure the examples described herein. Also, the description is not considered as limiting the scope of the examples described herein.

It will be appreciated that the examples and corresponding diagrams used herein are for illustrative purposes only. Different configurations and terminology can be used without departing from the principles expressed herein. For instance, components and modules can be added, deleted, modified, or arranged with differing connections without departing from these principles.

Although the above principles have been described with reference to certain specific examples, various modifications thereof will be apparent to those skilled in the art as outlined in the appended claims.

The invention claimed is:

1. A sole for footwear, the sole comprising
    a bottom surface, the bottom surface bisected by a lateral side and a medial side opposing the lateral side;
    a primary surface located on the lateral side; and
    one or more positioning faces located on the medial side;
    wherein the one or more positioning faces are at one or more angles to the primary surface respectively;
    wherein engaging a ground with the primary surface causes the footwear to provide a natural stance;
    wherein engaging the ground with the one or more positioning faces causes the footwear to be positioned in one or more athletic stances;
    wherein the one or more positioning faces comprise at least a first positioning face and a second positioning face,
    the first positioning face being located on the medial side under a big toe of the wearer, and
    the second positioning face being located on the medial side under the ball of the wearer's foot;
    wherein the first positioning face engaging the ground is curved radially outward and;
    wherein the second positioning face engaging the ground is sloped towards the medial side.

2. The sole of claim 1, wherein the positioning faces comprise an additional third positioning face.

3. The sole of claim 2, wherein the third positioning face is located under an arch of the wearer's foot.

4. The sole of claim 3, wherein any of the one or more positioning faces are subdivided into subfaces.

5. The sole of claim 4, wherein the athletic stances comprise a first athletic stance and a second athletic stance, wherein:
    the first athletic stance engages the ground with a first set of one or more positioning faces or subfaces; and
    the second athletic stance engages the ground with a second set of one or more positioning faces or subfaces.

6. The sole of claim 5, wherein the athletic stances result in one or more of the wearer's ankles remaining in a neutral position.

7. The sole of claim 6, wherein the one or more positioning faces engages with a transition mechanism to transition between the athletic stance and the natural stance.

8. The sole of claim 7, wherein the transition mechanism comprises a hinge and an outsole, such that the hinge is located in between the primary surface and the one or more positioning faces; and the outsole extends from the hinge towards at least one positioning face such that a space is created between the at least one positioning face and the outsole.

9. The sole of claim 8, wherein the space between the positioning face and the outsole is filled with a compressible material.

10. The sole of claim 8, wherein the transition mechanism comprises at least one of a lever, a wedge and a flap.

11. The sole of claim 10, wherein the bottom surface is partially covered with a cushion.

12. The sole of claim 11, wherein the bottom surface comprises a tread.

13. The sole of claim 12, wherein the bottom surface comprises flexible grooves.

14. The sole of claim 1, wherein any one or more of the positioning faces is revealed when a positioning face attachment member is detached from the bottom surface.

15. A plate for footwear, the plate comprising:
    a bottom surface, the bottom surface bisected by a lateral side and a medial side opposing the lateral side;
    a primary surface located on the lateral side; and
    one or more positioning faces located on the medial side;
    wherein the one or more positioning faces are at one or more angles to the primary surface respectively;
    wherein engaging a ground with the primary surface causes the footwear to provide a natural stance;

wherein engaging the ground with the one or more positioning faces causes the footwear to be positioned in one or more athletic stances;

wherein the one or more positioning faces comprise at least a first positioning face and a second positioning face, the first positioning face being located on the medial side under a big toe of the wearer, and the second positioning face being located on the medial side under the ball of the wearer's foot;

wherein the first positioning face engaging the ground is curved radially outward and;

wherein the second positioning face engaging the ground is sloped towards the medial side.

16. The plate of claim 15, further comprising a mechanism for attaching the one or more positioning faces to the primary surface; the mechanism comprising any of: a hook and loop fastener, mechanical fasteners, zippers, magnets, embedding or a combination of these mechanisms.

* * * * *